(12) United States Patent
Maeda et al.

(10) Patent No.: US 7,465,814 B2
(45) Date of Patent: *Dec. 16, 2008

(54) SULFONATE COMPOUND AND FLUORESCENT PROBE USING THE SAME

(75) Inventors: Hatsuo Maeda, Suita (JP); Norio Itoh, Suita (JP)

(73) Assignee: Osaka Industrial Promotion Organization, Osaka (JP)

( * ) Notice: Subject to any disclaimer, the term of this patent is extended or adjusted under 35 U.S.C. 154(b) by 104 days.

This patent is subject to a terminal disclaimer.

(21) Appl. No.: 11/328,744

(22) Filed: Jan. 10, 2006

(65) Prior Publication Data

US 2006/0105412 A1  May 18, 2006

Related U.S. Application Data

(63) Continuation of application No. PCT/JP2004/007751, filed on May 28, 2004.

(30) Foreign Application Priority Data

Jul. 11, 2003 (JP) .............................. 2003-273660

(51) Int. Cl.
C07D 265/34 (2006.01)
C07D 311/82 (2006.01)

(52) U.S. Cl. ....................... 549/223; 549/344; 549/388; 549/392; 549/393

(58) Field of Classification Search ................. 549/223, 549/344, 388, 392, 393
See application file for complete search history.

(56) References Cited

U.S. PATENT DOCUMENTS

| 4,618,622 A | 10/1986 | Schlecker et al. |
| 5,453,461 A | 9/1995 | Heiliger et al. |
| 5,576,424 A | 11/1996 | Mao et al. |
| 5,684,040 A | 11/1997 | Grabowski et al. |
| 5,986,094 A | 11/1999 | Ghoshal et al. |
| 6,130,101 A | 10/2000 | Mao et al. |

FOREIGN PATENT DOCUMENTS

| JP | 6-281581 | 10/1994 |
| JP | 2000-316598 | 11/2000 |
| WO | 98/39317 | 9/1998 |
| WO | 98/39319 | 9/1998 |

OTHER PUBLICATIONS

Maeda et al. J. Am. Chem. Soc., 2005, 127, 68-89.*
Nakano, M., "Detection of Active Oxygen Species in Biological Systems", Cellular and Molecular Neurobiology, vol. 18, No. 6, 1998, 565-579.
Murrant, et al., "Detection of Reactive Oxygen and Reactive Nitrogen Species in Skeletal Muscle", Microscopy Research and Technique, 55:236-248 (2001).
Tarpey, et al., "Methods of Detection of Vascular Reactive Species", Circ Res. 2001;89:224-236.
Münzel, et al., "Detection of Superoxide in Vascular Tissue", Arterioscler Thromb Vasc Biol. 2002;22:1761-1768.
Esposti, M.D., "Measuring mitochondrial reactive oxygen species", Methods 26 (2002) 335-340.
Rothe, et al., "Flow Cytometric Analysis of Respiratory Burst Activity in phagocytes with Hydroethidine and 2', 7'Dichlorofluorescin", Journal of Leukocyte Biology 47:440-448 (1990).
Carter, et al., "Intracellular hydrogen peroxide and superoxide anion detection in endothelial cells", Journal of Leukocyte Biology 55:253-258 (1994).
Bindokas, et al., "Superoxide Production in Rat Hippocampal Neurons: Selective Imaging with Hydroethidine", The Journal of Neuroscience, Feb. 15, 1996, 16(4): 1324-1336.
Al-Mehdi, et al., "Intracellular generation of reactive oxygen species during nonhypoxic lung ischemia", The American Physiological Society, 1997, 272, L294-L300.
Benov, et al., "Critical Evaluation of the Use of Hydroethidine as a Measure of Superoxide Anion Radical", Fee Radical Biology & Medicine, vol. 25, No. 7, pp. 829-831, 1998.
Fukuyama, et al., "2,4-Dinitrobenzenesulfonamides: A Simple and Practical Method for the Preparation of a Variety of Secondary Amines and Diamines", Tetrahedron Letters, vol. 38, No. 33, pp. 5831-5834, 1997.

(Continued)

Primary Examiner—Kahsay T Habte
(74) Attorney, Agent, or Firm—Hamre, Schumann, Mueller & Larson, P.C.

(57) ABSTRACT

The present invention provides a sulfonate compound, including a structure represented by a general formula (I) below,

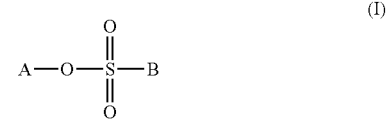

where, in the formula (I), an atomic group A-O is an atomic group that forms a fluorescent compound upon cleavage of a covalent bond between the atomic group A-O and a sulfonyl group, one or a plurality of atomic groups B—$SO_3$— are bonded to an atomic group A, B is a ring that is substituted by one or a plurality of electron-withdrawing groups, the electron-withdrawing group is at least one selected from the group consisting of an alkyl halide group, a nitro group and a cyano group, and B may be the same or different in kind in the case where the plurality of B exist.

6 Claims, 5 Drawing Sheets

OTHER PUBLICATIONS

Maeda, et al., "Hydrogen Peroxide-Induced Deacetylation of Acetyl Resorufin as a Novel Indicator Reaction for Fluorometric Detection of Glucose Using Only Glucose Oxidase", Chem. Pharm. Bull. 49(3) 294-298 (2001).

Maeda, et al., "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide", Chem. Pharm. Bull. 50(2) 169-174 (2002).

Maeda, et al., "Development of Fluorescent Probe Specific to Hydrogen Peroxide or Superoxide", on line Jul. 8, 2003, bmas lecture summery, Retrieval day Aug. 6, 2004, www10.showa-u.ac.jp/-bmas/proceedings/III-9.pdf (w/full translation).

Delzenne, et al., Photosensitive polymers I.-Synthesis and Properties of Coumarin-modified Polymers, Industrie Chimique Belge, 1967, 21, 373-378.

Esayan, et al., "Esters of sulfonic acids, SI. Synthesis and Acricidal Propertis of Some P-chlorobenzenesulfonic Acid Esters" Izvestiya akademii Nauk Armyanskoi SSR, Khimicheskie Nauki, 1962, vol. 15, 285-289.

Rendenbach-Müller, et al., "Synthesis of Coumarins as Subtype-Selective Inhibitors of Monoamine Oxidase", Bioorganic & Medicinal Chemistry Letter, vol. 4, No. 10, 1195-1198, 1994.

Matsu-ura, et al., "Blood glucose determination with an acetyl resorufin-glucose oxidase system as a fluorometirc indicator reaction", Bunseki Kagaku, vol. 50, No. 7, 475-479 (2001).

* cited by examiner

SULFONATE COMPOUND AND FLUORESCENT PROBE USING THE SAME

TECHNICAL FIELD

The present invention relates to a sulfonate compound and a fluorescent probe using the same.

BACKGROUND ART

It has been revealed that various diseases are caused by increased generation of active oxygen species in vivo. Thus, dynamic analyses of active oxygen species in vivo are important for clarifying the causes, the states and the like of diseases. In the analyses of active oxygen species, a bio-imaging method by a fluorescent probe plays a predominant role. Since the generation of superoxide is the root cause of the production of all of active oxygen species, the analyses thereof are very important. However, examples of the fluorescent probe for superoxide include only hydroethidium (HE) (Scheme 1 described below) (about HE, see, for example, (1) M. Nakano, Cell. Mol. Neurobiol. 1998, 18, 565-579; (2) C. L. Murrant, M. B. Reid, Microsc. Res. Tech. 2001, 55, 236-248; (3) M. M. Tarpey, I. Fridovich, Circ. Res. 2001, 89, 224-236; (4) T. Münzel, I. B. Afanas'ev, A. L. Klescchyov, D. G. Harrison, Arterioscler. Thromb. Vasc. Biol. 2002, 22, 1761-1768; (5) M. D. Esposti, Methods, 2002, 26, 335-340; (6) G. Rothe, G. Valet, J. Leukoc. Biol. 1990, 47, 440-448; (7) W. O. Carter, P. K. Narayanan, J. P. Robinson, J. Leukoc. Biol. 1994, 55, 253-258; (8) V. P. Bindokas, J. Jordán, C. C. Lee, R. J. Miller, J. Neurosci. 1996, 16, 1324-1336; (9) A. B. Al-Mehdi, H. Shuman, A. B. Fisher, Am. J. Pysiol. 1997, 272, L294-L300; (10) L. Benov, L. Sztejnberg, I. Fridovich, Free Radic. Biol. Med. 1998, 25, 826-831, etc.).

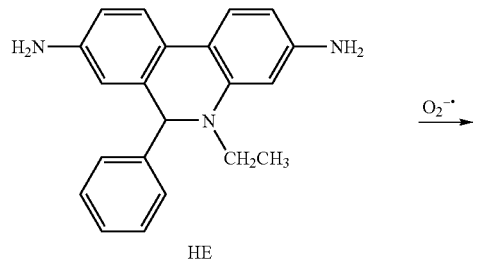

Scheme 1

HE $\xrightarrow{O_2^{-\bullet}}$

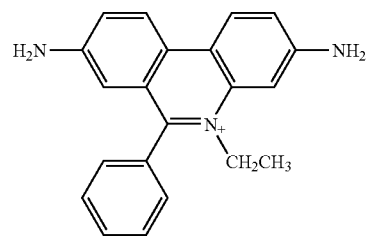

ethidium

Moreover, a fluorescence mechanism of HE is based on an oxidation reaction caused by superoxide, and thus has a problem in specificity (selectivity). That is, because many active oxygen species work as oxidizers, HE is oxidized also by other active oxygen species, and the magnitude of the oxidation is peroxynitrite>hydroxyl radical>superoxide>hydrogen peroxide, in this order. Furthermore, it is known that HE also is oxidized by cytochrome c. Therefore, it is thought that a fluorescence response obtained by using HE should be used, not as an indicator of an amount of generated superoxide, but as an indicator of a "total amount of oxidizers generated in vivo including active oxygen species". Whereas, examples of a probe based on a reducing power of superoxide include nitroblue tetrazolium (NBT). NTB is reduced by superoxide so as to be transformed into blue diformazane. However, an absorption probe of NBT has various problems that it is reduced by various kinds of reductase such as NOS, and the produced diformazane is transformed into NBT by disproportionation or oxidation, and moreover, the absorption probe of NBT cannot be used for leading-edge fluorescence analysis methods such as flow cytometry and confocal laser microscopes. With such a background, development of a fluorescent probe that responds to superoxide with high selectivity is required in the light of the cytophysiology and the like.

Whereas, assay methods including an acetyl cholinesterase (AChE) assay are important in the biochemical and medical fields of technologies. It is thought that a compound (a mercapto group-detecting compound) that can detect a compound having a mercapto group (a thiol group) can be used effectively for such essay methods. Several compounds having mercapto group-detectability actually have been developed so far, and they mainly are classified into the following three groups of types 1 to 3: the type 1 represents labeling reagents of fluorescent compounds; the type 2 represents fluorescence derivatizing agents for mercapto groups; and the type 3 represents coloring reagents based on reactions with mercapto groups. Examples of the compounds belonging to these types 1 to 3 and the general description of their mercapto group-detecting mechanisms will be shown respectively in Scheme 2 below.

Scheme 2

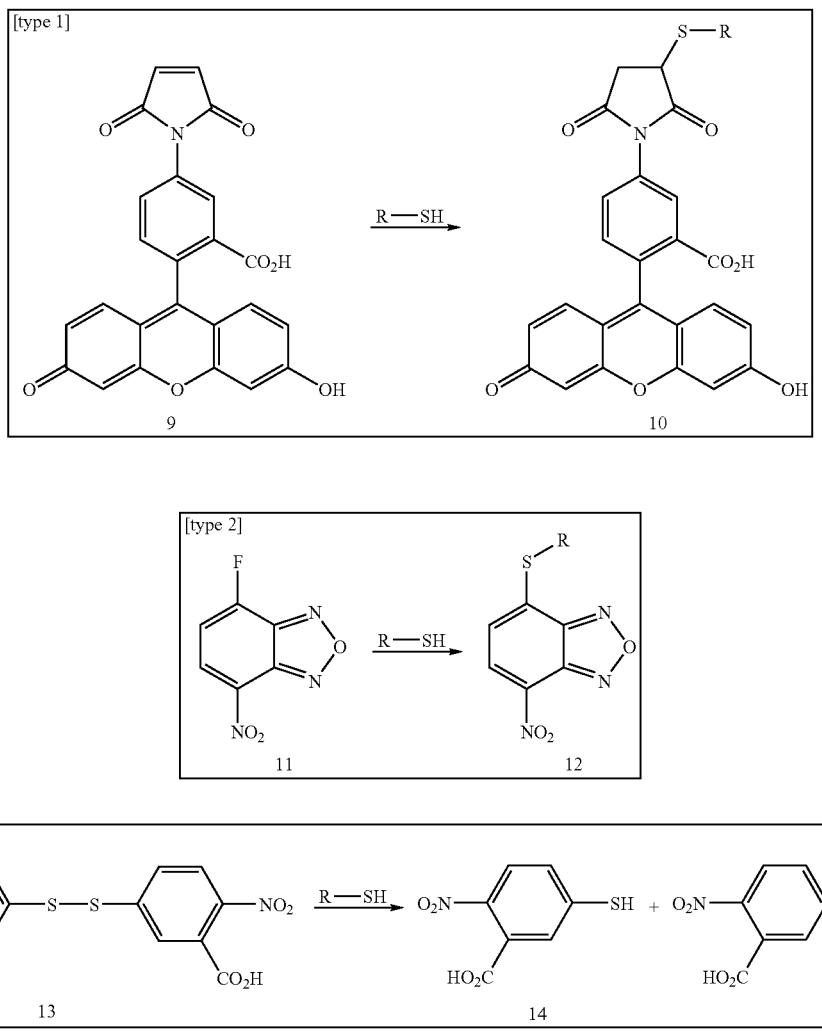

The reagent belonging to the type 1 such as the compound 9 is used only for synthesizing fluorescence-labeled protein or nucleic acid, and has a below-stated problem if being used for an AChE assay and the like. Firstly, the compound 9 is a fluorescent compound similar to its product 10. Accordingly, in the case of conducting an AChE assay or measurement of an AChE inhibitory activity by using the compound 9, the operational processes thereof are complicated because of the necessity to separate 9 and 10 after an enzyme reaction. Moreover, since maleimide that is a reaction part in 9 with a mercapto group reacts also with other nucleophilic reagents such as amines and alcohols, the reagent of the type 1 has a problem in specificity (selectivity).

Next, the reagent belonging to the type 2 such as the compound 11 is used only for a labeling agent for a separation analysis. The reagent 11 of the type 2 is non-fluorescent, and provides 12 that is a fluorochrome by reacting with a mercapto group. Thus, the operational process for separation with the reagent after the reaction is not necessary, unlike the case of 9. However, 11 also reacts with various nucleophilic agents so as to provide fluorescent compounds that are similar to 12, and thus has a problem if being used for an AChE assay and the like in terms of the specificity. However, 11 reacting with various nucleophilic agents is advantageous to be used as a labeling agent for the nucleophilic agents, and thus is used favorably for a labeling agent for HPLC analyses of amines and thiols.

The reagent 13 (an Ellman's reagent) of type 3 actually is used for an AChE assay. However, 13 has a problem of its poor stability in an aqueous solution, that is, low sensitivity caused by a high blank response.

As another example of the compound except the reagents of the types 1 to 3 that selectively reacts with thiol, a sulfonamide compound 15 that causes a deprotecting reaction with thiol is reported (Fukuyama, T., et al., Tetrahedron Lett., 1997, 38, 5831-5834). It also is reported that a nucleophilic aromatic substitution reaction of the compound 15 proceeds more smoothly with a thiol compound than with an amino compound. More specifically, in the case of an amino compound, it is necessary to use an amount thereof much larger than that of 15 and requires a long period of reaction time. However, none of the compound 15 and its product shows fluorescence, and thus they cannot be expected to be used as a thiol-detecting compound at all.

Scheme 3

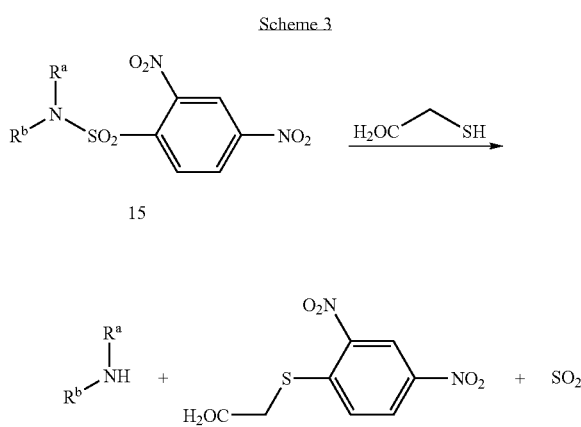

As mentioned above, in the light of the application of an AChE assay method using acetyl thiocholine as a substrate, as a more common method, the development of a new mercapto group-detecting compound to replace the compound 13 and the like has been required.

DISCLOSURE OF INVENTION

In the light of the above-stated conventional problems, it is an object of the present invention to provide a new organic compound that can be used for a fluorescent probe and the like responding to superoxide or a mercapto compound with high selectivity.

In order to attain the above-mentioned object, the present invention provides a sulfonate compound including a structure represented by a general formula (I) below.

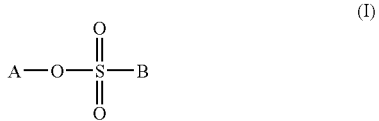

In the formula (I), an atomic group A-O is an atomic group that forms a fluorescent compound upon cleavage of a covalent bond between the atomic group A-O and a sulfonyl group, one or a plurality of atomic groups B—$SO_3$— are bonded to an atomic group A, B is a ring that is substituted by one or a plurality of electron-withdrawing groups, the electron-withdrawing group is at least one selected from the group consisting of an alkyl halide group, a nitro group and a cyano group, and B may be the same or different in kind in the case where the plurality of B exist.

The sulfonate compound of the present invention has the structure represented by the general formula (I), and thus can be used for a fluorescent probe having high selectivity that does not respond to hydroxyl radical or hydrogen peroxide but responds only to superoxide, a fluorescent probe that responds to a mercapto compound with high selectivity, or the like. Moreover, the fluorescent probe using the sulfonate compound of the present invention also can be used as a fluorescent probe that has low responses with respect to not only active oxygen species in a cell except superoxide, for example, hydroxyl radical and hydrogen peroxide, but also other physiological active materials, but responds to superoxide or a mercapto compound with high selectivity. Examples of the other physiological active material include: reducing compounds such as ascorbic acid and 1,4-hydroquinone; nucleophilic compounds such as glucose, propylamine and diethylamine; and reductase such as a cytochrome P450 reductase+NADPH system and a diaphorase+NADH system. Herein, a "mercapto compound" in the present invention represents a compound having a mercapto group (a —SH group) in general, and an atom to which a mercapto group is bonded may be a carbon atom or other arbitrary atom, for example, nitrogen, phosphorus or the like.

BRIEF DESCRIPTION OF DRAWINGS

FIG. 5 is a graph showing fluorescence responses with respect to glutathione and cysteine: FIG. 5A shows measurement results of the compound 6a; and FIG. 5B shows measurement results of the compound 8a.

FIG. 6 is a graph showing a relationship between an acetyl cholinesterase activity and a fluorescence response of the compound 8a.

FIG. 7 is a graph showing measurement results of acetyl cholinesterase inhibitory activities of neostigmine and pyridostigmine caused by the compound 8a.

DESCRIPTION OF THE INVENTION

Figure 1:
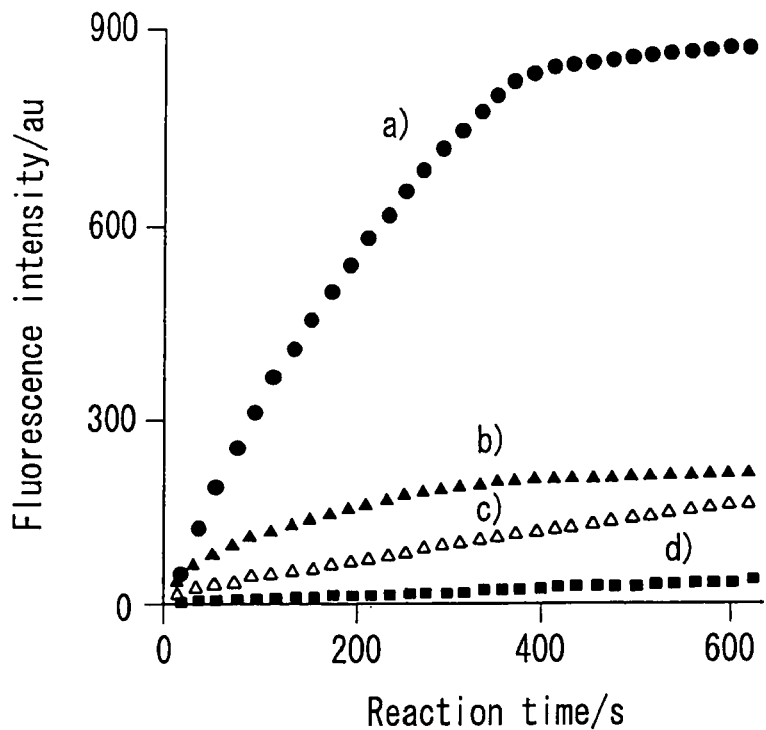
FIG. 1 is a graph showing superoxide-detectability of a compound 1d.

Firstly, features of the compound of the present invention in detection of superoxide will be described.

A conventional fluorescent probe HE is transformed into a fluorescent compound by an oxidation reaction. Thus, the conventional fluorescent probe HE has a problem in specificity, as mentioned above. Whereas, a fluorescent probe utilizing a fluorescence mechanism based on a reduction reaction does not exist, but NBT is exemplified as an absorption probe. In the case of NBT, its fluorescence mechanism is a simple reduction reaction, and thus a reverse reaction, that is, a reaction for transforming a generated colorant into NBT proceeds. On the other hand, a fluorescence mechanism of the compound of the above general formula (I) is not a simple oxidation-reduction reaction, but is based on a desulfonylation reaction that is induced by a nucleophilic aromatic substitution reaction, for example, Scheme 4 described below. That is, the mechanism is, for example, Scheme 4 described below. Herein, Scheme 4 is only an example of the mechanism, and does not limit the present invention.

Scheme 4

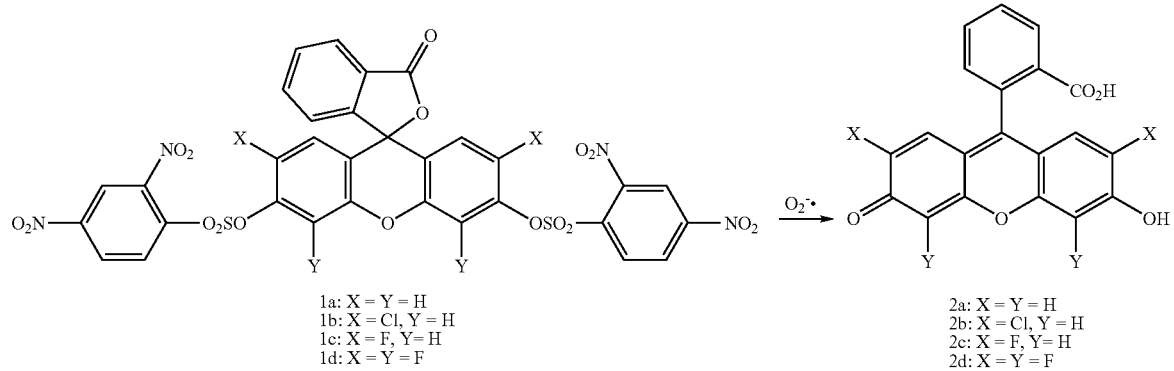

Therefore, it is thought that, according to the compound of the present invention represented by the above general formula (I), not only the problem of HE but also the reverse reaction of NBT can be avoided. The inventors of the present invention have designed and developed a fluorescent probe on the basis of such a fluorescence reaction for the first time.

A more specific mechanism of the reaction of Scheme 4 is assumed as, for example, Scheme 5 described below. Herein, Scheme 5 shows only an example of the presumed mechanism, and does not limit the present invention at all.

Scheme 5

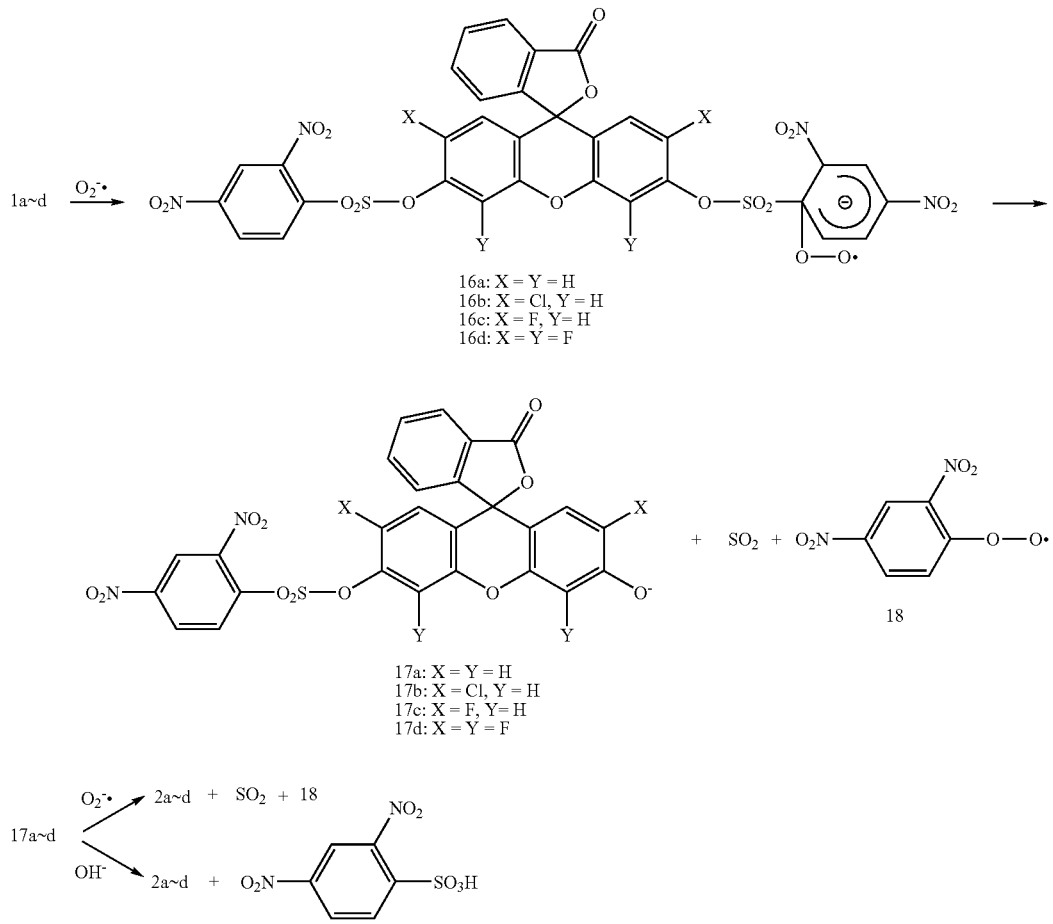

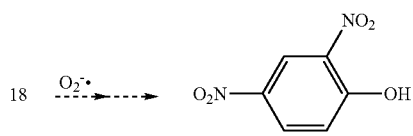

Next, features of the sulfonate compound of the present invention in the detection of a mercapto group are discussed.

The sulfonate compound of the present invention belongs to the above-described type 3 as a mercapto group-detecting compound, but has the following features in comparison with the existing reagents of types 1 to 3.

A fluorescence mechanism of the mercapto compound-responsive-type fluorescent probe of the present invention is assumed to be based on, for example, a nucleophilic aromatic substitution reaction represented by Scheme 6 below. Herein, Scheme 6 shows only an example of the presumed mechanism, and does not limit the present invention.

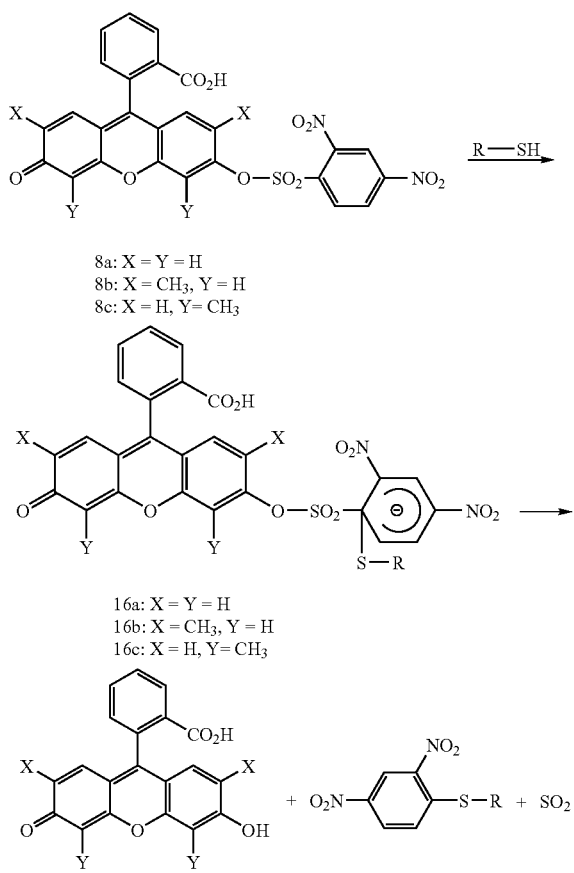

The fluorescence caused by such a reaction of a sulfonate compound like the compound of the present invention has not been reported yet. And, the compound of the present invention, as is represented by the above general formula (I), responds to a mercapto compound with higher specificity and higher selectivity in comparison with amino compounds and the like. Moreover, the compound of the present invention forms a fluorescent compound upon cleavage of the covalent bond between the atomic group A-O and the sulfonyl group, and thus also can detect a mercapto compound by simple operational processes without separating the compound and the like after the reaction. Therefore, an assay system that cannot be attained by the conventional mercapto compound-detecting reagents can be expected to be constructed by using the compound of the present invention.

Next, embodiments of the present invention will be described below.

The atomic group B in the above formula (I) is a ring substituted by one or a plurality of electron-withdrawing groups, as mentioned above, but preferably is an aromatic ring or a heteroaromatic ring that is substituted by one or a plurality of electron-withdrawing groups. This is because, if the ring forming the atomic group B is such an aromatic ring or a heteroaromatic ring, the detectablity is expected to be increased more when the compound of the present invention is used for a superoxide-detecting probe or a mercapto compound-detecting probe. More specifically, since it is thought that, for example, the reaction is not a simple nucleophilic substitution reaction as represented by Scheme 5 or 6 above, but is a nucleophilic aromatic substitution reaction, the detectability thereof is expected to be higher. The number of atoms in the atomic group B is not particularly limited, but the atomic group B may include a 5- to 18-membered ring, for example.

In the atomic group B in the formula (I), the electron-withdrawing group is preferably at least one selected from the group consisting of a straight or branched alkyl halide group having 1 to 6 carbon atoms, a nitro group and a cyano group. And, in the light of the detectablity and the like with respect to superoxide and a mercapto compound, the electron-withdrawing group more preferably includes at least one of a nitro group and a trifluoromethyl group, and still more preferably includes a nitro group. In addition, the atomic group B further may be substituted as necessary by an electron-withdrawing group other than an alkyl halide group, a nitro group and a cyano group, for example, a halogen atom or the like, and further may be substituted by an arbitrary group other than an electron-withdrawing group, for example, a methyl group, an isopropyl group, a methoxy group or the like. Moreover, in the atomic group B, the ring more preferably is at least one selected from the group consisting of: a benzene ring; a naphthalene ring; an anthracene ring; a pyrene ring; a pyridine ring; a pyrrole ring; a thiophene ring; a furan ring; a benzopyridine ring; a benzopyrrole ring; a benzothiophene ring; and a benzofuran ring.

It is more preferable that, in the light of the sensitivity of the fluorescent probe and the specificity (selectivity) thereof with respect to superoxide and a mercapto compound, the atomic group B is at least one selected from the group consisting of: a 2,4-dinitrophenyl group; a 4-nitrophenyl group; a 2-nitrophenyl group; a 2-nitro-(4-trifluoromethyl)phenyl group; a 2-nitro-4-methoxyphenyl group; a 4-nitro-2-methoxyphenyl group; a 2-nitro-4-methylphenyl group; a 4-nitro-2-methylphenyl group; a 2-nitro-4,6-dimethylphenyl group; a 4-nitro-2,6-dimethylphenyl group; a 2-nitro-4-chlorophenyl group; a 4-nitro-2-chlorophenyl group; and a 2-nitro-4-isopropylphenyl group. The atomic group B still more preferably is at least one selected from the group consisting of: a 2,4-dinitrophenyl group; a 2-nitro-(4-trifluoromethyl)phenyl group; a 2-nitro-4-methoxyphenyl group; a 4-nitro-2-methoxyphenyl group; a 2-nitro-4-methylphenyl group; a 4-nitro-2-methylphenyl group; a 2-nitro-4,6-dimethylphenyl group; a 4-nitro-2,6-dimethylphenyl group; a 2-nitro-4-chlorophenyl group; a 4-nitro-2-chlorophenyl group; and a 2-nitro-4-isopropylphenyl group, and particularly preferably is a 2,4-dinitrophenyl group, but may be various kinds of groups other than these.

In the case where the compound of the present invention is used for a probe for detecting a certain material, its responses with respect to other materials preferably are suppressed to be as low as possible, in the light of the specificity (selectivity). However, the possibility for the compound to be used for a probe for detecting the certain material is not eliminated by its ability thereof to respond to other materials except the certain material, and the compound can be used appropriately for detecting the certain material by setting measurement conditions appropriately or the like. By molecular-designing the sulfonate compound of the present invention appropriately within a range represented by the above formula (I), a sulfonate compound that shows high specificity with respect to any of superoxide and a mercapto compound can be obtained. In addition, the specificity (selectivity) of the fluorescent probe using the sulfonate compound of the present invention is not limited particularly, but preferably is as follows, for example. That is, a fluorescence response with respect to superoxide or a mercapto compound is preferably 10 times or more, more preferably is 20 times or more, and particularly preferably is 100 times or more than that with respect to hydrogen peroxide. An upper limitation value of the fluorescence response with respect to superoxide or a mercapto compound is not limited particularly, but generally is, for example, 1000 times or lower than that with respect to hydrogen peroxide. Moreover, the fluorescence response with respect to superoxide or a mercapto compound is preferably 10 times or more, more preferably is 20 times or more, and particularly preferably is 100 times or more than that with respect to hydroxyl radical, glucose, ascorbic acid, 1,4-hydroquinone, propylamine or diethylamine. An upper limitation value thereof is not limited particularly, but is, for example, 1000 times or lower than that with respect to any of these materials. The fluorescence response with respect to superoxide or a mercapto compound preferably is 4 times or more, more preferably is 5 times or more, still more preferably 10 times, and particularly preferably 20 times or more than that with respect to a cytochrome P450 reductase+NADPH system or a diaphorase+NADH system. An upper limitation value thereof is not limited particularly, but generally is, for example, 100 times or lower than that with respect to any of these systems. Herein, these values are obtained by comparing superoxide or a mercapto compound with the above-described respective materials in equimolar amounts, where a measurement temperature is 37° C., an excitation wavelength is 485±20 nm, and an emission wavelength is 530±20 nm. However, the conditions of the measurement using the fluorescent probe of the present invention are not limited to these, and may be any measurement conditions.

In the case where the sulfonate compound of the present invention is used for a superoxide-detecting probe, in the light of the specificity (selectivity), a sulfonate compound in which a plurality of atomic groups B—SO$_3$— are bonded to the atomic group A in the above formula (I) is used preferably. In this case, the electron-withdrawing group in the atomic group B in the above formula (I) more preferably includes at least one of a nitro group and a trifluoromethyl group, and still more preferably includes a nitro group. Still further preferably, the atomic group B is at least one selected from the group consisting of: a 2,4-dinitrophenyl group; a 4-nitrophenyl group; a 2-nitrophenyl group; a 2-nitro-(4-trifluoromethyl)phenyl group; a 2-nitro-4-methoxyphenyl group; a 4-nitro-2-methoxyphenyl group; a 2-nitro-4-methylphenyl group; a 4-nitro-2-methylphenyl group; a 2-nitro-4,6-dimethylphenyl group; a 4-nitro-2,6-dimethylphenyl group; a 2-nitro-4-chlorophenyl group; a 4-nitro-2-chlorophenyl group; and a 2-nitro-4-isopropylphenyl group. Still further more preferably, the atomic group B is at least one selected from the group consisting of a 2,4-dinitrophenyl group; a 2-nitro-(4-trifluoromethyl)phenyl group; a 2-nitro-4-methoxyphenyl group; a 4-nitro-2-methoxyphenyl group; a 2-nitro-4-methylphenyl group; a 4-nitro-2-methylphenyl group; a 2-nitro-4,6-dimethylphenyl group; a 4-nitro-2,6-dimethylphenyl group; a 2-nitro-4-chlorophenyl group; a 4-nitro-2-chlorophenyl group; and a 2-nitro-4-isopropylphenyl group, and it particularly preferably is a 2,4-dinitrophenyl group. In addition, in the case where a sulfonate compound in which one atomic group B—SO$_3$— is bonded to the atomic group A in the above formula (I) is used for a superoxide-detecting probe, it is preferable that the electron-withdrawing group in the atomic group B in the above formula (I) includes only one nitro group, in the light of the superoxide selectivity. Examples of such an atomic group B include a 2-nitrophenyl group and a 4-nitrophenyl group as mentioned above, and groups derived from them. However, needless to say, the other sulfonate compounds according to the present invention besides them also can be used for a superoxide-detecting fluorescent probe.

In addition, in the case where the sulfonate compound of the present invention is used for a mercapto compound-detecting probe, it is preferable that one atomic group B—SO$_3$— is bonded to the atomic group A in the above formula (I), in the light of the specificity (selectivity). In this case, in terms of the higher specificity, mercapto compound-detectability and the like, the electron-withdrawing group in the atomic group B in the above formula (I) more preferably includes a nitro group, and particularly preferably includes a plurality of nitro groups. For example, in the above formula (I), the atomic group B still more preferably is at least one selected from the group consisting of: a 2,4-dinitrophenyl group; a 4-nitrophenyl group; a 2-nitrophenyl group; a 2-nitro-(4-trifluoromethyl)phenyl group; a 2-nitro-4-methoxyphenyl group; a 4-nitro-2-methoxyphenyl group; a 2-nitro-4-methylphenyl group; a 4-nitro-2-methylphenyl group; a 2-nitro-4,6-dimethylphenyl group; a 4-nitro-2,6-dimethylphenyl group; a 2-nitro-4-chlorophenyl group; a 4-nitro-2-chlorophenyl group; and a 2-nitro-4-isopropylphenyl group. Still further more preferably, the atomic group B is at least one selected from the group consisting of: a 2,4-dinitrophenyl group; a 2-nitro-(4-trifluoromethyl)phenyl group; a 2-nitro-4-methoxyphenyl group; a 4-nitro-2-methoxyphenyl group; a 2-nitro-4-methylphenyl group; a 4-nitro-2-methylphenyl group; a 2-nitro-4,6-dimethylphenyl group; a 4-nitro-2,6-dimethylphenyl group; a 2-nitro-4-chlorophenyl group; a 4-nitro-2-chlorophenyl group; and a 2-nitro-4-isopropylphenyl group, and particularly preferably is a 2,4-dinitrophenyl group. However, needless to say, other sulfonate compounds besides them also can be used for a mercapto compound-detecting probe.

In the atomic group A-O in the above formula (I) in the sulfonate compound of the present invention, for example, the O atom preferably is bonded directly to an aromatic ring or a heteroaromatic ring, in terms of the higher detectability and the like when being used for a fluorescent probe. The number of atoms constituting the aromatic ring or the heteroaromatic ring is not particularly limited, but the aromatic ring or the heteroaromatic ring may be a 5- to 30-membered ring, for example. It is preferable that, in the sulfonate compound of the present invention, a fluorescent compound formed upon cleavage of the covalent bond between the atomic group A-O and the sulfonyl group is at least one selected from the group consisting of: fluorescein; resorufin; 7-hydroxycoumarin; 1-naphthol; 2-naphthol; 1-hydroxyanthracene; 2-hydroxyanthracene; 9-hydroxyanthracene; 1-hydroxypyrene; 1-hydroxyacridine; 2-hydroxyacridine; 9-hydroxyacridine; 2-hydroxyquinolone; 4-hydroxyquinolone; 5-hydroxyquinolone; 6-hydroxyquinolone; 8-hydroxyquinolone; 4-hydroxy-7-nitro-2-oxa-1,3-diazole; and derivatives of them, but is not limited to them, and may be any fluorescent compounds. Moreover, in the case where the fluorescent compound is 7-hydroxycoumarin or a derivative of 7-hydroxycoumarin other than 7-hydroxy-4-(trifluoromethyl)coumarin, the atomic group B more preferably is at least one selected from the group consisting of: a 2,4-dinitrophenyl group; a 2-nitro-(4-trifluoromethyl)phenyl group; a 2-nitro-4-methoxyphenyl group; a 4-nitro-2-methoxyphenyl group; a 2-nitro-4-methylphenyl group; a 4-nitro-2-methylphenyl group; a 2-nitro-4,6-dimethylphenyl group; a 4-nitro-2,6-dimethylphenyl group; a 2-nitro-4-chlorophenyl group; a 4-nitro-2-chlorophenyl group; and a 2-nitro-4-isopropylphenyl group. It is still more preferable that the derivative of fluorescein is a derivative obtained by substituting at least one of a 2-position, a 4-position, a 5-position and a 7-position of the fluorescein by a straight or branched alkyl group having 1 to 6 carbon atoms or a halogen, and the derivative of 7-hydroxycoumarin is a derivative obtained by substituting a 4-position of the 7-hydroxycoumarin by a straight or branched alkyl group having 1 to 6 carbon atoms or a trifluoromethyl group. Specific examples of a compound that is particularly preferable as the fluorescent compound formed upon cleavage of the covalent bond between the atomic group A-O and the sulfonyl group includes fluorescein, 2,7-dichlorofluorescein, 2,7-difluorofluorescein, 4,5-difluorofluorescein, 2,4,5,7-tetrafluorofluorescein, 2,7-dimethylfluorescein, 4,5-dimethylfluorescein, 2,4,5,7-tetramethylfluorescein, 2,7-diisopropylfluorescein, 2,7-di-t-butylfluorescein, 2,7-dimethoxyfluorescein, 2,4-difluoro-5,7-dimethylfluorescein, resorufin, 2,8-dichlororesorufin, 7-hydroxy-4-(trifluoromethyl)coumarin and 7-hydroxy-4-methylcoumarin.

Next, the sulfonate compound of the present invention preferably is represented by any of formulae (i) to (iv) below, for example.

(i)

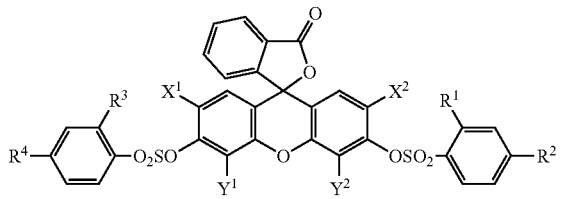

(ii)

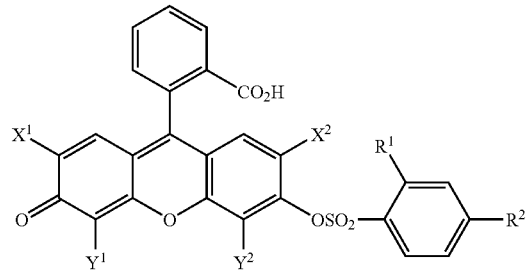

(iii)

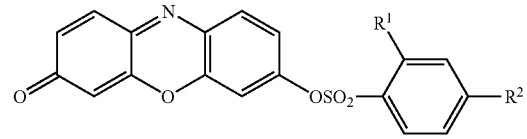

(iv)

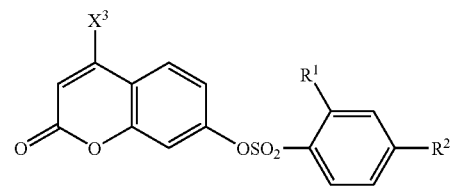

In the formulae (i) to (iv), each of $X^1$, $X^2$, $Y^1$ and $Y^2$ is a hydrogen atom, a straight or branched alkyl group having 1 to 6 carbon atoms or a halogen, $X^1$, $X^2$, $Y^1$ and $Y^2$ may be the same or different, $X^3$ is a straight or branched alkyl group having 1 to 6 carbon atoms or a trifluoromethyl group, each of $R^1$ and $R^3$ is a hydrogen atom, a nitro group, a methyl group, a chloro group or a methoxy group, $R^1$ and $R^3$ may be the same or different, each of $R^2$ and $R^4$ is a hydrogen atom, a nitro group, a trifluoromethyl group, a methyl group, an isopropyl group, a chloro group or a methoxy group, $R^2$ and $R^4$ may be the same or different, at least one of $R^1$ and $R^2$ is a nitro group, at least one of $R^3$ and $R^4$ is a nitro group, and in the case where, in the formula (Iv), $X^3$ is a straight or branched alkyl group having 1 to 6 carbon atoms, both of $R^1$ and $R^2$ are groups except a hydrogen atom.

In the case of being used for a mercapto compound-detecting probe, it is preferable that the sulfonate compound of the present invention is represented by any of the above formulae (ii) to (iv), and both of $R^1$ and $R^2$ are nitro groups.

Particularly preferable examples of the sulfonate compound of the present invention include a compound represented by any of formulae 1 and 3 to 8 below.

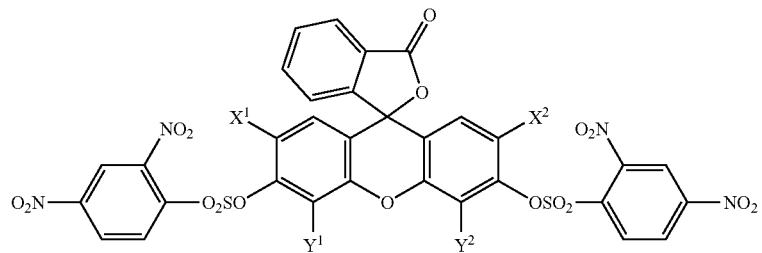

1

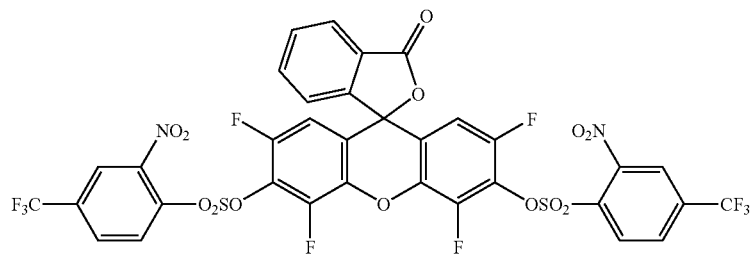

3

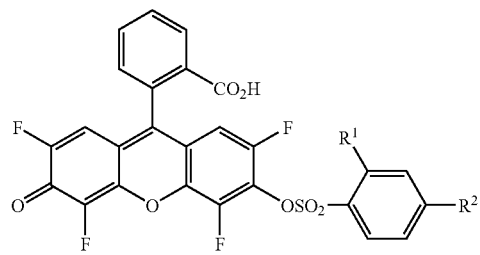

4

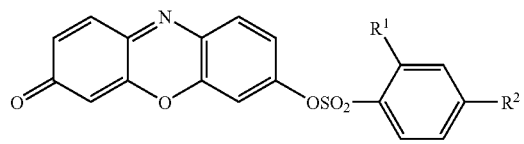

5

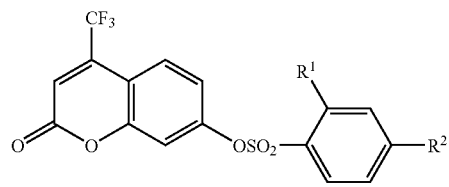

6

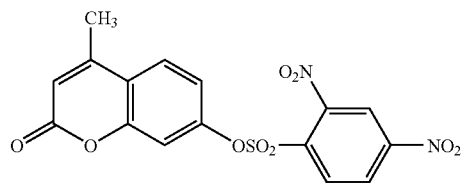

7

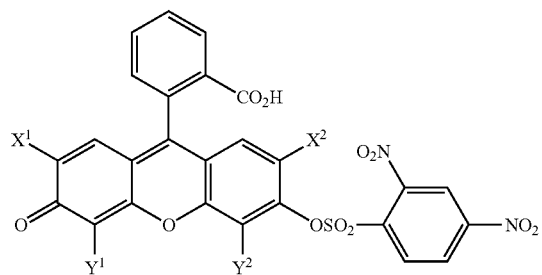

8

In the formulae 1 and 8, each of $X^1$, $X^2$, $Y^1$ and $Y^2$ is a hydrogen atom, a methyl group or a halogen, $X^1$, $X^2$, $Y^1$ and $Y^2$ may be the same or different, in the formulae 4, 5 and 6, $R^1$ is a hydrogen atom, a nitro group, a methyl group, a chloro group or a methoxy group, $R^2$ is a hydrogen atom, a nitro group, a trifluoromethyl group, a methyl group, an isopropyl group, a chloro group or a methoxy group, and at least one of $R^1$ and $R^2$ is a nitro group.

Among them, in the case of being used for a superoxide-detecting probe, the sulfonate compound represented by any of formulae 1a to 1d, 3, 4a to 4e, 5a, 5b, 6a and 6b below is particularly preferable, and in the case of being used for a mercapto compound-detecting probe, the sulfonate compound represented by any of formulae 5a, 6a, 7, 8a, 8b and 8c below is particularly preferable.

1a: X = Y = H
1b: X = Cl, Y = H
1c: X = F, Y = H
1d: X = Y = F

4a: R¹ = NO₂, R² = CF₃
4b: R¹ = H, R² = NO₂
4c: R¹ = NO₂, R² = H
4d: R¹ = NO₂, R² = OCH₃
4e: R¹ = OCH₃, R² = NO₂

5a: R¹ = NO₂, R² = NO₂
5b: R¹ = NO₂, R² = CF₃

6a: R¹ = NO₂, R² = NO₂
6b: R¹ = NO₂, R² = CF₃

8a: X = Y = H
8b: X = CH₃, Y = H
8c: X = H, Y = CH₃

A method for manufacturing the sulfonate compound of the present invention represented by the general formula (I) above is not limited particularly, and a known manufacturing method for a sulfonate compound and the like may be used as appropriate. For example, the sulfonate compound of the present invention can be manufactured by a manufacturing method including a step of combining a compound represented by a formula (II) below and a compound represented by a formula (III) below.

$$A\!-\!OH \quad (II)$$

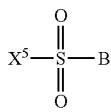
(III)

In the formula (III), $X^5$ is a halogen, and A and B are the same as A and B in the above formula (I). As the compound of the above formula (II), for example, the above-described fluorescent compound and the like may be used, and preferable examples of the fluorescent compound are as described above. More specifically, the compound of the formula (II) may be, for example, fluorochromes such as fluorescein, derivatives of fluorescein, 7-hydroxy-4-(trifluoromethyl)coumarin and 7-hydroxy-4-methylcoumarin, which will be represented by below formulae, but is not limited to them, and various compounds can be used.

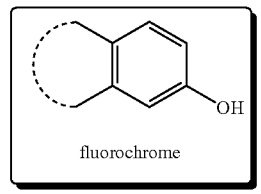
fluorochrome

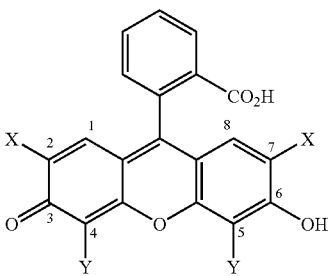
fluorescein

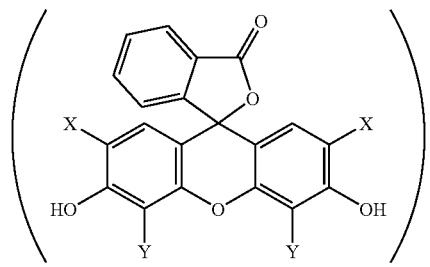

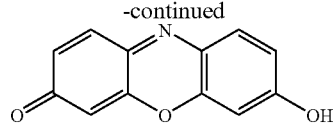
resorufin

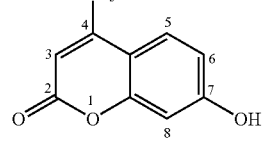
7-hydroxy-4-(trifluoromethyl)coumarin

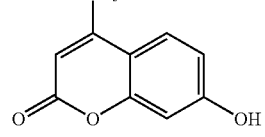
7-hydroxy-4-methylcoumarin

Herein, in the present invention, a "halogen" represents an arbitrary halogen atom, and may be, for example, fluorine, chlorine, bromine or iodine. An alkyl halide group is not limited particularly, but may be, for example, a group that is obtained by halogenating a methyl group, an ethyl group, a n-propyl group, an isopropyl group, a n-butyl group, an isobutyl group, a sec-butyl group, a tert-butyl group or the like, respectively. The alkyl halide group preferably is, for example, a perfluoro alkyl group, more preferably is a straight or branched perfluoro alkyl group having 1 to 6 carbon atoms, more specifically is a perfluoro alkyl group that is derived from an alkyl group, for example, a methyl group, an ethyl group, a n-propyl group, an isopropyl group, a n-butyl group, an isobutyl group, a sec-butyl group, a tert-butyl group or the like, and particularly preferably is a trifluoromethyl group.

In the case where the compound represented by the above formula (I) has an isomer such as a tautomer, a stereoisomer and an optical isomer, the isomer also is included as the compound of the present invention. Moreover, in the case where any of the compound of the formula (I) and the other compounds according to the present invention can form a salt, the salt also is included as the compound of the present invention. The salt is not limited particularly, and may be, for example, an acid addition salt or a base addition salt. Furthermore, an acid for forming the acid addition salt may be an inorganic acid or an organic acid, and a base for forming the base addition salt may be an inorganic base or an organic base. The inorganic acid is not limited particularly, but may be, for example, sulfuric acid, phosphoric acid, hydrochloric acid, hydrobromic acid, hydriodic acid or the like. The organic acid also is not limited particularly, but may be, for example, p-toluenesulfonic acid, methanesulfonic acid, oxalic acid, p-bromobenzenesulfonic acid, carbonic acid, succinic acid, citric acid, benzoic acid, acetic acid or the like. The inorganic base is not limited particularly, but may be, for example, ammonium hydroxide, alkali metal hydroxides, alkaline-earth metal hydroxides, carbonates, hydrogencarbonates or the like, and more specifically is, for example, sodium hydroxide, potassium hydroxide, potassium carbonate, sodium carbonate, sodium hydrogen carbonate, potassium hydrogen carbonate, calcium hydroxide, calcium carbonate or the like. The organic base also is not limited particularly, but may be, for example, ethanolamine, triethylamine, tris-(hydroxymethyl)aminomethane or the like.

A method for manufacturing the salt of the compound of the present invention also is not limited particularly, and may be, for example, adding the above-described acids or bases to the compound of the present invention appropriately by a known method.

The fluorescent probe of the present invention shows high selectivity with respect to superoxide or a mercapto compound, by including the sulfonate compound of the present invention. Thus, since the fluorescent probe of the present invention has excellent sensitivity and accuracy, the fluorescent probe of the present invention, or a superoxide-detecting method or a mercapto compound-detecting method using the same is suitable for being applied to, for example, a bio-imaging method and the like. Accordingly, the sulfonate compound of the present invention also is used suitably for a reagent for a clinical analysis and the like.

In addition, a configuration of the sulfonate compound of the present invention is not limited by its application purpose, but preferably is selected appropriately according to its application purpose. In the case where the compound of the present invention is used for a superoxide-detecting fluorescent probe or a mercapto compound-detecting probe, compounds that are preferable for each of the application purposes in terms of the specificity (selectivity) are as described above. The fluorescent probe of the present invention can have high specificity (selectivity) and detectability with respect to superoxide or a mercapto compound, by including these compounds of the present invention.

The fluorescent probe of the present invention is used suitably for bio-imaging and the like as mentioned above, but also may be used for various purposes other than this. An application purpose of the superoxide-detecting fluorescent probe of the present invention is not limited particularly, but it is suitable for, for example, an assay method using blotting (transcription), a superoxide dismutase quantitative method, a superoxide scavenging ability measurement method for functional food or a pharmaceutical, a clinical analysis method, a screening method for a pharmaceutical, and the like. Moreover, an application purpose of the mercapto compound-detecting fluorescent probe of the present invention is not limited particularly, but it is suitable for, for example, a kinase assay method; an acetyl cholinesterase assay method; an assay method using blotting (transcription); a clinical analysis method; and a screening method for a pharmaceutical. These methods will be described below more specifically.

The assay method using blotting (transcription) represents an assay method including a step of detecting, by using the fluorescent probe of the present invention, a material that is blotted (transcribed) on a support. Its operational processes and the like are not limited particularly, and any known methods can be used appropriately, as long as they allow the material to react with the fluorescent probe of the present invention on the support. The support also is not limited particularly, and, for example, a known matter such as agarose gels, polyacrylamide gels, nitrocellulose films and nylon films may be used. For example, by appropriately designing a kit including the fluorescent probe of the present invention and the support, the kit may be used for the assay method using blotting.

Next, a superoxide quantitative method using the superoxide-detecting fluorescent probe of the present invention is conducted by comparing fluorescence responses that respectively are obtained after the reactions effected in the presence of a sample containing the superoxide dismutase and in the absence of the sample. For example, a superoxide dismutase concentration in a human or animal body fluid can be measured by a method including conducting the superoxide dismutase quantitative method by using, as the sample containing superoxide dismutase, the human or animal body fluid or a sample obtained by extracting the body fluid. Moreover, the superoxide dismutase quantitative method also can be applied to superoxide scavenging ability measurement of functional food and a pharmaceutical, for example. More specifically, the superoxide scavenging ability of functional food or a pharmaceutical can be measured by a method including: a step of measuring a superoxide dismutase concentration in a human or animal body fluid by the superoxide dismutase quantitative method; a step of administering the functional food or the pharmaceutical with the human being or the animal, subsequently; and a step of measuring a superoxide dismutase concentration in the human or animal body fluid again by the superoxide dismutase quantitative method after the administration. For example, by assay with respect to a human being or an animal using these measurement methods, screening of a pharmaceutical for a treatment for a disease related to superoxide, prevention of such a disease or relief of its phenomena also can be carried out. And, a kit suitable for such measurement methods can be obtained by designing a kit including the superoxide-detecting probe of the present invention as appropriate.

Next, a kinase assay method using the mercapto compound-detecting probe of the present invention includes, for example, a step of thiophosphorylating a substrate by using kinase and γ-S-ATP; and a step of detecting the thiophosphorylated substrate by using the mercapto compound-detecting probe of the present invention. As the substrate, for example, protein can be used. More specifically, protein usually is phosphorylated by using kinase and ATP, but by using γ-S-ATP instead of ATP, protein can be thiophosphorylated. Moreover, by detecting the thus thiophosphorylated protein by using the mercapto compound-detecting probe of the present invention, a kinase assay method can be conducted. It is preferable that the kinase assay method further include a step of separating the kinase from a sample by using an antibody. A kit suitable for this kinase assay method can be obtained by appropriately designing a kit including, for example, the mercapto compound-detecting probe of the present invention, γ-S-ATP and a substrte, and it is preferable that the kit further includes an antibody of kinase.

Next, an acetyl cholinesterase assay method using the mercapto compound-detecting fluorescent probe of the present invention includes, for example, a step of producing thiocholine by a reaction between acetyl thiocholine and acetyl cholinesterase; and a step of detecting the thiocholine by using the mercapto compound-detecting fluorescent probe of the present invention. A kit for this acetyl cholinesterase assay can be obtained by appropriately designing a kit including the mercapto compound-detecting fluorescent probe of the present invention and acetyl thiocholine.

The description of a typical kinase assay and a typical acetyl cholinesterase (AChE) assay, and advantages of the kinase assay and the acetyl cholinesterase (AChE) assay of the present invention will be provided below.

In the case of an enzyme such as AChE and kinase, an activity level thereof, rather than an expression level thereof, has a closer relationship to a physiological phenomenon.

Development of these simple enzyme activity assay methods are very important from the clinical point of view, and besides, they have much significance in terms of the development of new pharmaceuticals. More specifically, a measurement method of enzyme activities can be used not only as a method for diagnosing a state of a certain disease, but also as a method for screening an enzyme inhibitor as seeds of new pharmaceuticals. In either of the cases of using as the diagnostic method and the screening method, the assay method preferably is a method that is simple in operation, requires a short period of time for measurement, and is friendly for the environment.

As one of conventionally used AChE or kinase assay methods, a radioassay using a substrate of acetyl choline (labeled with $^3$H) or ATP (labeled with $^{32}$P) that is labeled with RI is exemplified. This method has an advantage of high sensitivity, but also has a problem in terms of the influence on the environment because of using RI. As another method of the AChE assay, a method using an Ellman's reagent is exemplified, but it has a problem with sensitivity as mentioned above.

Moreover, as a kinase assay method with a nonradioactivity technique, an enzyme immunoassay has been used conventionally. There are two ways of operational processes for this enzyme immunoassay. Those are: (1) phosphorylation of an immobilized substrate>>an antigen-antibody reaction of an enzyme modified antibody with the phosphorylated substrate>>washing>>coloration or chemiluminescence caused by the enzyme reaction>>detection; and (2) phosphorylation of an immobilized substrate>>an antigen-antibody reaction of a biotin modified antibody with the phosphorylated substrate>>washing>>complex formation with an avidin modified antibody>>washing>>coloration or chemiluminescence caused by the enzyme reaction>>detection. These methods have a problem of requiring a modified antibody that is specific to each phosphorylated substrate.

Advantages of the kinase assay and the acetyl cholinesterase (AChE) assay of the present invention will be described below. Firstly, their operational processes are simple. Specifically, in the AChE assay, an enzyme reaction and a fluorescence reaction can proceed at the same time. And, in the kinase assay, measurement can be conducted in simple processes by effecting an enzyme reaction and thereafter a fluorescence reaction, and also can be conducted by using only an enzyme substrate and a probe as reagents. Moreover, it can be expected that detection sensitivity of the measurement method using the mercapto compound-detecting fluorescent probe of the present invention can be equivalent to that of chemiluminescence.

By assaying with respect to a human being or an animal by using the acetyl cholinesterase assay method or the kinase assay method of the present invention, for example, screening of a pharmaceutical for a treatment for a disease related to acetyl choline or kinase, prevention of the disease or relief of a symptom of the disease also can be carried out. The disease related to acetyl choline or kinase is not limited particularly, but examples thereof include: cancers; an Alzheimer's disease; hypertension; angina pectoris; arteriosclerotic diseases such as myocardial infarction; inflammatory diseases such as arthritis; and various kinds of metabolic diseases.

By assaying with respect to a human being or an animal by using the superoxide-detecting probe and the mercapto compound-detecting probe of the present invention that are described above, various clinical analysis methods can be carried out. Thus, the sulfonate compound of the present invention is used suitably for a reagent for a clinical analysis as mentioned above, and by setting a kit including this reagent for the clinical analysis as appropriate, a kit for a clinical analysis that is used suitably for various purposes can be obtained.

The sulfonate compound of the present invention also can be used for manufacturing a mercapto compound-detecting fluorescent probe. Moreover, the sulfonate compound of the present invention also can be used for manufacturing a kinase-assaying fluorescent probe, an acetyl cholinesterase-assaying fluorescent probe or a fluorescent probe used for a blotting method.

The present invention will be described more specifically below, by way of Examples. However, these Examples are only exemplification of the present invention, and the present invention is not limited to these.

EXAMPLE 1

In the present example, the compounds 1a to 1d, 3, 4a, 4b, 5a, 5b, 6a and 6b were synthesized, and moreover, the capability of each of these compounds as a superoxide-detecting fluorescent probe was evaluated. Furthermore, application tests for a cell system also were carried out.

(Measurement Conditions etc.)

Nuclear magnetic resonance (NMR) spectra were measured by using EX-270 (trade name) (at 270 MHz during measurement of $^1$H) manufactured by JEOL as a measurement apparatus. Chemical shifts are shown in part per million (ppm). Tetramethylsilane (TMS) was used for an internal standard of 0 ppm. A coupling constant (J) is shown in hertz, and codes of s, d, t, q, m and br denote a singlet, a doublet, a triplet, a quartet, a multiplet and a broad, respectively. Mass spectroscopy (MS) was conducted by high resolution mass spectrometry (HRMS)/a fast atom bombardment (FAB), using JMS-700 (trade name) manufactured by JEOL. Infrared absorption (IR) spectra were measured by a KBr method using VALOR-III (trade name) manufactured by JASCO Corporation. Elementary analyses were conducted by using CHN CORDER MT-5 (trade name) manufactured by Yanaco. Melting points were measured by using MP-S3 (trade name) manufactured by Yanaco. Fluorescence intensity measurement was conducted by using a CytoFluor II multiwell fluorescence plate reader (trade name) manufactured by PerSeptive Biosystems, Inc. in the U.S. by setting an excitation filter and an emission filter at 485±20 nm and 530±25 nm respectively, unless otherwise stated. For column-chromatography separation, silica gel (manufactured by Merk & Co., Inc., Silica gel 60 (trade name)) was used. All chemicals were in reagent grade, and each of them was purchased from any of ALDRICH, LANCASTER GROUP AG, Tokyo Kasei Kogyo Co., Ltd., Nacalai Tesque, Inc. and Wako Pure Chemical Industries, Ltd.

(Synthesis)

[Syntheses of 1a to 1d]

The compounds 1a to 1d were synthesized in the same manner. Firstly, fluoresceins 2a to 2d that respectively corresponded to the compounds 1a to 1d were provided. Specifically, 2a and 2b were commercially available products, and 2c and 2d were synthesized by a method described in W.-C. Sun, K. R. Gee, D. H. Klaubert, R. P. Haungland, J. Org. Chem. 1997, 62, 6469-6475. Next, 2,6-lutidine (5.0 mL) was added to a suspension of each of these fluoresceins (1.0 g) and 2,4-dinitrobenzenesulfonyl chloride (2.2 eq) in dichloromethane (20 mL) at 0° C. The obtained mixed solution was stirred at room temperature for 4 to 6 hours. The reaction solution was diluted with dichloromethane (200 mL), was washed with 1M hydrochloric acid (200 mL×2) and saturated saline (200 mL), and was dried over magnesium sulfate. The residue obtained by evaporating the solvent under a reduced pressure was refined by silica gel column-chromatography (dichloromethane), thereby obtaining each objective compound. Yields and instrumental analytical values of the compounds 1a to 1d will be described below.

1a: 1.4 g (59%) as slightly yellow powder. m.p. 131-135° C. $^1$H-NMR (270 MHz, d$_6$-DMSO, TMS): δ=9.11 (d, $^4J_{H,H}$=2.3 Hz, 2H; aromatic), 8.62 (dd, $^3J_{H,H}$=8.6 Hz, $^4J_{H,H}$=2.3 Hz, 2H; aromatic), 8.36 (d, $^3J_{H,H}$=8.6 Hz, 2H; aromatic), 8.05 (d, $^3J_{H,H}$=7.3 Hz, 1H; aromatic), 7.85-7.73 (m, 2H, aromatic), 7.39-7.36 (m, 3H; aromatic), 7.00-6.98 (m, 4H; aromatic). FTIR (KBr): ν=1770 (CO, s), 1557 (NO$_2$, s), 1541 (NO$_2$, s) cm$^{-1}$. FAB HRMS calcd for C$_{32}$H$_{17}$N$_4$O$_{17}$S$_2$ (MH$^+$): 793.0030; found: 793.0017.

1b: 1.0 g (47%) as slightly yellow powder. m.p. 199-202° C. $^1$H-NMR (270 MHz, d$_6$-DMSO, TMS): δ=9.12 (d, $^4J_{H,H}$=2.1 Hz, 2H; aromatic), 8.66 (dd, $^3J_{H,H}$=8.7 Hz, $^4J_{H,H}$=2.1 Hz, 2H; aromatic), 8.43 (d, $^3J_{H,H}$=8.7 Hz, 2H; aromatic), 8.05 (d, $^3J_{H,H}$=7.4 Hz, 1H; aromatic), 7.86-7.74 (m, 2H, aromatic), 7.59 (s, 2H; aromatic), 7.43 (d, $^3J_{H,H}$=7.4 Hz, 1H; aromatic), 7.23 (s, 2H; aromatic). FTIR (KBr): ν=1773 (CO, s), 1558 (NO$_2$, s), 1541 (NO$_2$, s) cm$^{-1}$. Elemental analysis (%) calcd for C$_{32}$H$_{14}$Cl$_2$N$_4$O$_{17}$S$_2$: C, 44.61; H, 1.64; N, 6.50; found: C, 44.54; H, 1.82; N, 6.27. FAB HRMS calcd for C$_{32}$H$_{15}$Cl$_2$N$_4$O$_{17}$S$_2$ (MH$^+$): 860.9251; found: 860.9221.

1c: 1.5 g (67%) as a white crystal. m.p. 140-146° C. (from AcOEt). $^1$H-NMR (270 MHz, d$_6$-DMSO, TMS): δ=9.13 (d, $^4J_{H,H}$=2.0 Hz, 2H; aromatic), 8.66 (dd, $^3J_{H,H}$=8.7 Hz, $^4J_{H,H}$=2.0 Hz, 2H; aromatic), 8.43 (d, $^3J_{H,H}$=8.7 Hz, 2H; aromatic), 8.04 (d, $^3J_{H,H}$=7.3 Hz, 1H; aromatic), 7.85-7.32 (m, 2H, aromatic), 7.58 (d, $^4J_{H,F}$=6.3 Hz, 2H; aromatic), 7.43 (d, 3$J_{H,H}$=7.4 Hz, 1H; aromatic), 7.13 (d, $^3J_{H,F}$=10.2 Hz, 2H; aromatic). FTIR (KBr): ν=1774 (CO, s), 1557 (NO$_2$, s), 1542 (NO$_2$, s) cm$^{-1}$. Elemental analysis (%) calcd for C$_{32}$H$_{14}$F$_2$N$_4$O$_{17}$S$_2$—C$_4$H$_8$O$_2$: C, 47.17; H, 2.42; N, 6.11; found: C, 47.20; H, 2.47; N, 6.03. FAB HRMS calcd for C$_{32}$H$_{15}$F$_2$N$_4$O$_{17}$S$_2$ (MH$^+$): 828.9842; found: 828.9847.

1d: 1.1 g (51%) as a white crystal. m.p. 155-160° C. (from AcOEt-hexane). $^1$H-NMR (270 MHz, CDCl$_3$, TMS): δ=8.74 (d, $^4J_{H,H}$=2.1 Hz, 2H; aromatic), 8.63 (dd, $^3J_{H,H}$=8.7 Hz, $^4J_{H,H}$=2.1 Hz, 2H; aromatic), 8.40 (d, $^3J_{H,H}$=8.7 Hz, 2H; aromatic), 8.09 (d, $^3J_{H,H}$=6.9 Hz, 1H; aromatic), 7.83-7.72 (m, 2H, aromatic), 7.21 (d, $^3J_{H,H}$=7.4 Hz, 1H; aromatic), 6.52 (dd, $^3J_{H,F}$=9.3 Hz, $^4J_{H,F}$=2.1 Hz, 2H; aromatic). FTIR (KBr): ν=1775 (CO, s), 1558 (NO$_2$, s), 1542 (NO$_2$, s) cm$^{-1}$. Elemental analysis (%) calcd for C$_{32}$H$_{12}$F$_4$N$_4$O$_{17}$S$_2$: C, 44.45; H, 1.64; N, 6.48; found: C, 44.35; H, 1.64; N, 6.24. FAB HRMS calcd for C$_{32}$H$_{13}$F$_4$N$_4$O$_{17}$S$_2$ (MH$^+$): 864.9653; found: 864.9625.

[Synthesis of 3]

2,6-lutidine (5.0 mL) was added to a suspension of tetrafluorofluorescein 2d (1.0 g) and 2-nitro-4-(trifluoromethyl)benzenesulfonyl chloride (2.2 eq) in dichloromethane (20 mL) at 0° C. The obtained mixed solution was stirred at room temperature for 4 hours. The reaction solution was diluted with dichloromethane (200 mL), was washed with 1M hydrochloric acid (200 mL×2) and saturated saline (200 mL), and was dried over magnesium sulfate. The residue obtained by evaporating the solvent under a reduced pressure was refined by silica gel column-chromatography (dichloromethane), thereby obtaining the objective compound. A yield and instrumental analytical values of this compound will be described below.

3: 2.1 g (92%) as a white crystal. m.p. 138-142° C. (from AcOEt). $^1$H-NMR (270 MHz, d$_6$-DMSO, TMS): δ=8.84 (s, 2H; aromatic), 8.47 (d, $^3J_{H,H}$=8.4 Hz, 2H; aromatic), 8.40 (d, $^3J_{H,H}$=8.4 Hz, 2H; aromatic), 8.05 (d, $^3J_{H,H}$=6.9 Hz, 1H; aromatic), 7.86-7.74 (m, 2H, aromatic), 7.46 (d, $^3J_{H,H}$=7.4 Hz, 1H; aromatic), 7.15 (dd, $^3J_{H,F}$=10.2 Hz, $^4J_{H,F}$=2.1 Hz, 2H; aromatic). FTIR (KBr): ν=1776 (CO, s), 1557 (NO$_2$, s) cm$^{-1}$. Elemental analysis (%) calcd for C$_{34}$H$_{12}$F$_{10}$N$_2$O$_{13}$S$_2$·C$_4$H$_8$O$_2$: C, 45.70; H, 2.02; N, 2.81; found: C, 45.56; H, 1.82; N, 2.73. FAB HRMS calcd for C$_{34}$H$_{13}$F$_{10}$N$_2$O$_{13}$S$_2$ (MH$^+$): 910.9699; found: 910.9674.

[Syntheses of 4a and 4b]

The compounds 4a and 4b were synthesized in the same manner. Firstly, 2,6-lutidine (1.1 eq) was added to a suspension of tetrafluorofluorescein 2d (2.0 g) and 2-nitro-4-(trifluoromethyl)benzenesulfonyl chloride or 4-nitrobenzenesulfonyl chloride (1.1 eq) in dichloromethane (20 mL) at 0° C. Next, the obtained mixed solution was stirred at room temperature for 4 hours. The reaction solution was diluted with dichloromethane (200 mL), was washed with 1M hydrochloric acid (200 mL) and saturated saline (200 mL), and was dried over magnesium sulfate. The residue obtained by evaporating the solvent under a reduced pressure was refined by silica gel column-chromatography (dichloromethane-acetone=20:1), thereby obtaining each objective compound. Yields and instrumental analytical values of the compounds 4a and 4b will be described below.

4a: 0.72 g (22%) as yellow powder. m.p. 118-135° C. (from AcOEt-hexane). $^1$H-NMR (270 MHz, CD$_3$CN, TMS): δ=8.36 (d, $^4J_{H,H}$=1.2 Hz, 1H; aromatic), 8.32 (d, $^3J_{H,H}$=8.2 Hz, 1H; aromatic), 8.19-7.99 (m, 1H; aromatic), 7.82-7.70 (m, 2H; aromatic), 7.27-7.24 (m, 1H; aromatic), 6.68 (dd, $^3J_{H,F}$=10.1, $^3J_{H,H}$=2.4 Hz, 1H; aromatic), 6.49 (dd, $^3J_{H,F}$=10.1 Hz, $^4J_{H,F}$=2.4 Hz, 2H; aromatic). FTIR (KBr): ν=3208 (OH, br), 1766 (CO, s), 1557 (NO$_2$, s) cm$^{-1}$. FAB HRMS calcd for C$_{27}$H$_{11}$F$_7$NO$_9$S (MH$^+$): 658.0043; found: 658.0040.

4b: 0.6 g (21%) as yellow powder. m.p. 245-250° C. (from AcOEt-hexane). $^1$H-NMR (270 MHz, CD$_3$CN, TMS): δ=8.45-8.40 (m, 2H; aromatic), 8.24-8.20 (m, 2H; aromatic), 8.02-7.99 (m, 1H; aromatic), 7.82-7.70 (m, 2H; aromatic), 7.27-7.23 (m, 1H; aromatic), 6.64 (dd, $^3J_{H,F}$=10.1, $^3J_{H,H}$=2.3 Hz, 1H; aromatic), 6.47 (dd, $^3J_{H,F}$=10.9 Hz, $^4J_{H,F}$=2.3 Hz, 2H; aromatic)). FTIR (KBr): ν=3183 (OH, br), 1747 (CO, s), 1538 (NO$_2$, s) cm$^{-1}$. Elemental analysis (%) calcd for C$_{26}$H$_{11}$F$_4$NO$_9$S: C, 52.98; H, 1.88; N, 2.38; found: C, 53.01; H, 2.15; N, 2.23. FAB HRMS calcd for C$_{26}$H$_{12}$F$_4$NO$_9$S (MH$^+$): 590.0169; found: 590.0161.

[Syntheses of 5a and 5b]

The compounds 5a and 5b were synthesized in the same manner. Firstly, 2,4-dinitrobenzenesulfonyl chloride or 2-nitro-4-(trifluoromethyl)benzenesulfonyl chloride (1.1 eq) was added to a suspension of a resorufin sodium salt (2.0 g) corresponding to each of 5a and 5b in pyridine (20 mL) at −40° C. Next, the obtained mixed solution was stirred at −40° C. to −20° C. for 4 hours. The reaction solution was diluted with dichloromethane (200 mL), was washed with 1M hydrochloric acid (200 mL×2) and saturated saline (200 mL), and was dried over magnesium sulfate. The residue obtained by evaporating the solvent under a reduced pressure was refined by silica gel column-chromatography (dichloromethane-acetone=20:1), thereby obtaining each objective compound. Yields and instrumental analytical values of these compounds will be described below.

5a: 0.9 g (24%) as an orange crystal. m.p. 213-215° C. (from benzene). $^1$H-NMR (270 MHz, [D]$_6$DMSO, TMS): δ=9.13(s, 1H; aromatic), 8.62 (d, $^3J_{H,H}$=8.7 Hz, 1H; aromatic), 8.34 (d, $^3J_{H,H}$=8.7 Hz, 1H; aromatic), 7.90 (d, $^3J_{H,H}$=8.7 Hz, 1H; aromatic), 7.55 (d, $^3J_{H,H}$=9.8 Hz, 1H; aromatic), 7.47 (s, 1H, aromatic), 7.25 (d, $^3J_{H,H}$=8.7 Hz, 1H; aromatic), 6.85 (d, $^3J_{H,H}$=9.8 Hz, 1H; aromatic), 6.29 (s, 1H;

aromatic). FTIR (KBr): ν=1622 (CO, s), 1558 (NO$_2$, s), 1517 (NO$_2$, s) cm$^{-1}$. Elemental analysis (%) calcd for C$_{18}$H$_9$N$_3$O$_9$S: C, 48.76; H, 2.05; N, 9.48, S, 7.23; found: C, 48.88; H, 2.27; N, 9.26; S, 7.17.

5b: 1.2 g (30%) as an orange crystal. m.p. 204-207° C. (from AcOEt). $^1$H-NMR (270 MHz, CDCl$_3$, TMS): δ=8.35 (d, $^3J_{H,H}$=8.1 Hz, 1H; aromatic), 8.15 (s, 1H; aromatic), 8.01 (d, $^3J_{H,H}$=8.1 Hz, 1H; aromatic), 7.81 (d, $^3J_{H,H}$=8.4 Hz, 1H; aromatic), 7.42 (d, $^3J_{H,H}$=9.7 Hz, 1H; aromatic), 7.27-7.23 (m, 2H, aromatic), 6.87 (dd, $^3J_{H,F}$=9.7, $^3J_{H,H}$=2.0 Hz, 1H; aromatic), 6.33 (d, $^4J_{H,H}$=2.0 Hz, 1H; aromatic). FTIR (KBr): ν=1647 (CO, s), 1561 (NO$_2$, s) cm$^{-1}$. Elemental analysis (%) calcd for C$_{19}$H$_9$F$_3$N$_2$O$_7$S: C, 48.93; H, 1.95; N, 6.01; found: C, 48.75; H, 2.05; N, 5.76. FAB HRMS calcd for C$_{19}$H$_{10}$F$_3$N$_2$O$_7$S (MH$^+$): 467.0161; found: 467.0149.

[Syntheses of 6a and 6b]

The compounds 6a and 6b were synthesized in the same manner. Firstly, triethylamine (1.1 eq) was added to a suspension of 7-hydroxy-4-(trifluoromethyl)coumarin (1.0 g) and 2,4-dinitrobenzenesulfonyl chloride or 2-nitro-4-(trifluoromethyl)benzenesulfonyl chloride (1.1 eq) in dichloromethane (20 mL) at 0° C. Next, the obtained mixed solution was stirred at room temperature for 1 hour. The reaction solution was diluted with dichloromethane (200 mL), was washed with 1M hydrochloric acid (200 mL) and saturated saline (200 mL), and was dried over magnesium sulfate. The residue obtained by evaporating the solvent under a reduced pressure was refined by silica gel column-chromatography (dichloromethane), thereby obtaining each objective compound. Yields and instrumental analytical values of these compounds will be described below.

6a: 1.9 g (95%) as a white crystal. m.p. 123-124.5° C. (from benzene). $^1$H-NMR (270 MHz, [D]$_6$-DMSO, TMS): δ=9.13 (d, $^4J_{H,H}$=2.3 Hz, 1H; aromatic), 8.64 (dd, $^3J_{H,H}$=8.7 Hz, $^4J_{H,H}$=2.3 Hz, 1H; aromatic), 8.35 (d, $^3J_{H,H}$=8.7 Hz, 1H; aromatic), 7.79 (dd, $^3J_{H,H}$=8.9 Hz, $^3J_{H,H}$=1.5 Hz, 1H; aromatic), 7.54 (d, $^4J_{H,H}$=2.5 Hz, 1H, aromatic), 7.32 (dd, $^3J_{H,H}$=8.9, $^4J_{H,H}$=2.5 Hz, 1H; aromatic), 7.15 (s, 1H; aromatic). FTIR (KBr): ν=1751 (CO, s), 1558 (NO$_2$, s), 1542 (NO$_2$, s) cm$^{-1}$. Elemental analysis (%) calcd for C$_{16}$H$_7$F$_3$N$_2$O$_9$S: C, 41.75; H, 1.53; N, 6.09; found: C, 41.74; H, 1.63; N, 5.92. FAB HRMS calcd for C$_{16}$H$_8$F$_3$N$_2$O$_9$S (MH$^+$): 460.9903; found: 460.9888.

6b: 2.0 g (95%) as a white crystal. m.p. 134.5-136° C. (from AcOEt-hexane). $^1$H-NMR (270 MHz, [D]$_6$-DMSO, TMS): δ=8.82 (s, 1H; aromatic), 8.33 (d, $^4J_{H,H}$=1.5 Hz, 2H; aromatic), 7.83 (dd, $^3J_{H,H}$=8.9 Hz, $^4J_{H,H}$=1.8 Hz, 1H; aromatic), 7.57 (t, $^4J_{H,H}$=2.2 Hz, 1H; aromatic), 7.34 (dt, $^3J_{H,H}$=8.9 Hz, $^4J_{H,H}$=2.2 Hz, 1H, aromatic), 7.15 (s, 1H; aromatic). FTIR (KBr): ν=1752 (CO, s), 1557 (NO$_2$, s) cm$^{-1}$. Elemental analysis (%) calcd for C$_{17}$H$_7$F$_6$NO$_7$S: C, 42.25; H, 1.46; N, 2.90; found: C, 42.24; H, 1.55; N, 2.72. FAB HRMS calcd for C$_{17}$H$_8$F$_6$NO$_7$S (MH$^+$): 483.9926; found: 483.9925.

(Evaluation as Superoxide-Selective Fluorescent Probe)

The reactivity of the compounds 1a to 1d with superoxide was examined, and it was found that all of the compounds showed fluorescence responses by reacting with superoxide, but among them, 1d was particularly superior in sensitivity and the like. Then, by mainly using the compound 1d as a testing compound, the capability thereof as a superoxide-selective fluorescent probe was evaluated, and moreover, a test in a cell system also was conducted. These tests will be described below.

[1-1. Reactivity with Respect to Superoxide]

Reactivity of the compound 1d with superoxide was tested as follows. The compound 1d (0.25 mmol) was allowed to react with KO$_2$ (5 eq) in a mixed solution containing DMSO and a 10 mM HEPES buffer solution having a pH of 7.4 (1:1), at room temperature for 10 minutes, then fluorescence caused by the derivative of the fluorescein 2d was identified. As a result of the analysis of the product, it was found that 1d had been consumed completely, and moreover, 0.24 mmol of 2,4-dinitrophenol was isolated. The product was identified by comparing its $^1$H-NMR, IR and mass spectra with those of a commercially available compound. A reaction mechanism thereof is not clear, but is assumed to be Scheme 7 described below, for example. Regardless of the presence of a highly excessive amount of KO$_2$, an amount of 2,4-dinitrophenol generated was about 1 equivalent to that of 1d, and thus it also can be assumed that a second elimination reaction (a transformation reaction from 17d to 2d) was not a reaction with superoxide but proceeded by another mechanism. Herein, Scheme 7 is only an example of the mechanism that can be estimated with respect to the compound 1d by the above-described conditions, and does not limit the present invention.

Scheme 7

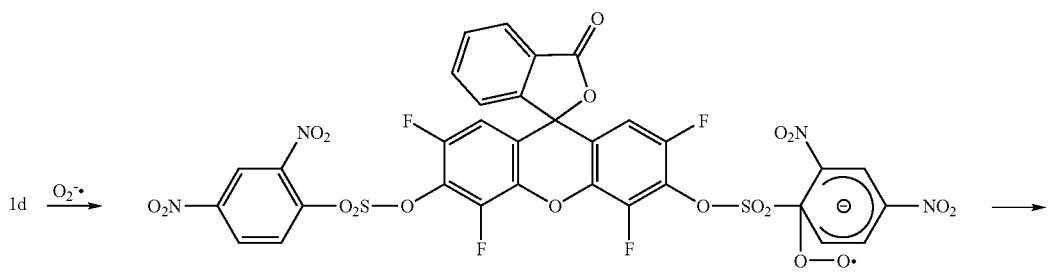

16d

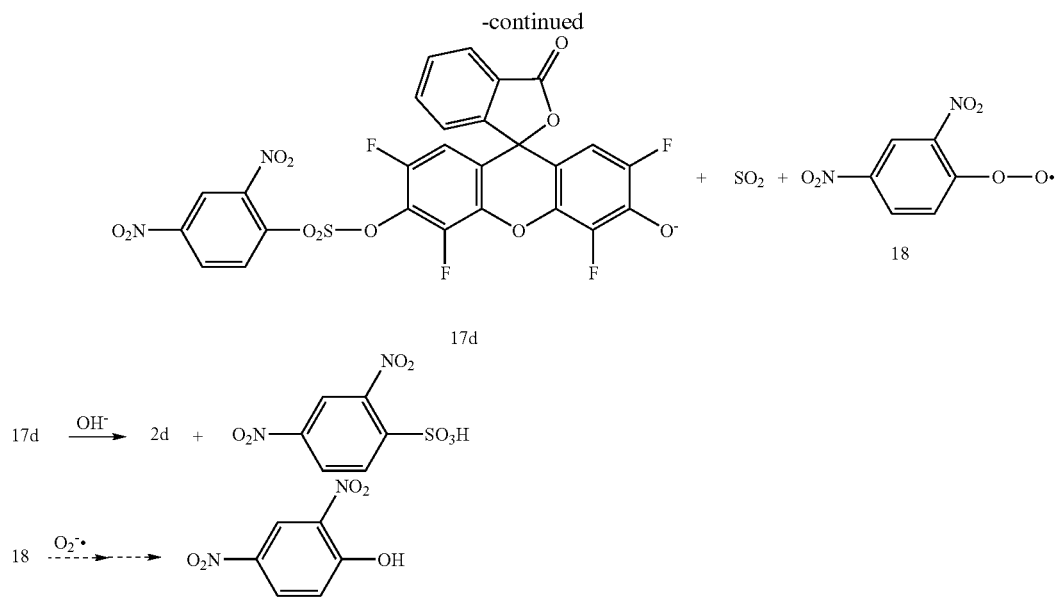

[1-2. Superoxide-Selectivity (1)]

Firstly, the capability of the compound 1d as a superoxide-selective fluorescent probe was tested, and it was found that 1d has excellent specificity with respect to superoxide. FIG. 1 shows results of the test. This figure is a graph showing results that are obtained by tracking fluorescence by allowing the compound 1d to react with $H_2O_2$ or superoxide produced enzymatically, a horizontal axis thereof represents a reaction time (second), and a vertical axis thereof represents a fluorescence intensity (au). In the figure, (a) represents a result obtained by a reaction in the presence of HPX and XO, (b) represents a result obtained by a reaction in the presence of HPX, XO and SOD, (c) represents a result obtained by a reaction under an anaerobic condition in the presence of HPX, XO and SOD, and (d) represents a result obtained by a reaction with only $H_2O_2$. The test results shown in FIG. 1 will be described below in further detail.

Firstly, from the fact that, as shown in FIG. 1(a), 1d reacted with superoxide generated from the hypoxanthine (HPX)/xanthine oxidase (XO) system so as to increase a fluorescence response significantly in a short period of time, it was found that 1d has high sensitivity with respect to superoxide. More specifically, the enzyme reaction of the compound 1d (16 μM), xanthine oxidase (XO, 0.01 U/mL) and hypoxanthine (HPX, 40 μM) at 37° C. in a HEPES buffer solution (pH 7.4, 10 mM, 2.5 mL) was tracked at an excitation wavelength of 511 nm and an emission wavelength of 531 nm, then a fluorescent response caused by the formation of the compound 2d (above Scheme 4) was observed, and a progressive curve shown in FIG. 1(a) was obtained. In addition, since a similar test was conducted except further adding superoxide dismutase (SOD) (40 U/mL), then a fluorescence response was inhibited significantly as shown in FIG. 1(b), it was confirmed that the fluorescence response shown in FIG. 1(a) was caused by superoxide.

And, as shown in FIG. 1(d), the reaction between the compound 1d and $H_2O_2$ (40 μM) caused an increase of a fluorescence intensity that is small enough to be neglected. Therefore, it was shown that 1d shows only a small response with respect to hydrogen peroxide, and thus has excellent specificity with respect to superoxide.

Moreover, from the result shown in FIG. 1(c), it was found that the compound 1d has an advantage, compared with nitroblue tetrazolium (NBT) that is a conventional superoxide-detecting agent. A specific description thereof will be provided below. NBT has a property of being reduced by superoxide $O^{2-•}$, and thus is used for a probe for spectrophotometric measurement and the like. However, NBT has a serious problem of being reduced not only by superoxide but also by reductase that exists in a biosystem. Thus, it was tested whether detection of $O^{2-•}$ by the compound 1d also had a similar problem or not, by effecting the enzyme reaction by using the compound 1d, XO, HPX and SOD under the anaerobic condition, and then the production of 2d from 1d that was caused by a XO reductant proceeded at a very low speed, as shown in FIG. 1(c). This result is in marked contrast to an observation result that a reduction from NBT to formazan by a xanthine-XO system proceeded at a higher speed in an anaerobic condition than in an aerobic condition. As mentioned above, it was shown that, in the detection of $O^{2-•}$ based on the fluorescence by using the compound 1d, complication caused by intracellular reductase can be eliminated or suppressed significantly.

[1-3. Superoxide-Selectivity (2)]

Moreover, in other conditions than those of the above-described tests, reactivity of all of the compounds 1a to 1d with $H_2O_2$, other various kinds of nucleophilic agents, reducing agents and the like also was tested, respectively. More specifically, fluorescent responses of 1a to 1d with respect to a XO-HPX system, a XO-HPX-SOD system, $H_2O_2$, ascorbic acid, 1,4-hydroquinone, propylamine, diethylamine, glucose, esterase, a cytochrome P450 reductase+NADPH system, and a diaphorase+NADH system were measured, respectively. Operational processes thereof will be described below. Firstly, 1a to 1d and the above-described reagents were dissolved in HEPES of 10 mM having a pH of 7.4 so as to prepare solutions, respectively. Next, a 96 wellmicroplate was provided, where any of the solutions of 1a to 1d (25 μM, 170 μL) was poured into each of the wells, and furthermore, 30 μL of a blank solution or 30 μL of the solution of the reagent to be reacted therewith was added thereto. Final concentrations of the solutions in the wells were adjusted so that concentrations of the solutions of 1a to 1d respectively could be 21.3 μM, that of XO could be 13.1 mU/mL, those of HPX, $H_2O_2$, ascorbic acid, 1,4-hydroquinone, propylamine, diethylamine, glucose, NADPH and NADH respectively could be 50 μM, that of cytochrome P450 reductase could be 68 mU/mL, that of diaphorase could be 65 mU/mL, and that of esterase could be 0.5 U/mL, respectively. Then, after they reacted in the wells at 37° C. for 10 minutes, fluorescent responses were measured respectively. Fluorescence intensity measurement was conducted by using an ETC-272 Peltier thermostatted single cell holder (trade name) manufactured by JASCO Corporation or a SpectraMax GeminiEM fluorescence plate reader (trade name) manufactured by Molecular Devices Corporation provided with a FP-750 spectrofluorometer (trade name) manufactured by JASCO Corporation, and by setting excitation wavelengths and emission wavelengths so that those of 1a, 1b and 1c respectively could be 485 nm and 515 nm, and those of 1d respectively could be 511 nm and 540 nm. As shown in Table 1 below, from the results with respect to the XO-HPX system and the XO-HPX-SOD system, it was found that all of 1a to 1d showed responses with respect to superoxide with high sensitivity, but did not show any response with respect to $H_2O_2$, ascorbic acid, 1,4-hydroquinone, propylamine, diethylamine and glucose, and showed only neglectably small responses with respect to esterase, respectively. Also, in the cytochrome P450 reductase+NADPH system, and in the diaphorase+NADH system, none of 1a to 1d showed a response that is enough large to affect the superoxide detection. Since each of 1a, 1b, 1c and 1d showed a cathode response at about −0.5 V vs SCE in voltammetry measurement in $CH_3CN$—$H_2O$ (3:1) containing $Et_4NClO_4$, it was expected that the superoxide detection was inhibited by reduction by intracellular reductase except superoxide, but contrary to such an expectation, 1a, 1b, 1c and 1d showed high selectivity with respect to superoxide, as mentioned above.

TABLE 1

Comparison of the respective fluorescent responses of 1a, 1b, 1c and 1d with respect to the various kinds of biological reactants and the enzyme systems.

| biological reactant or enzyme system | fluorescent response | | | |
|---|---|---|---|---|
| | 1a | 1b | 1c | 1d |
| blank | 10 | 10 | 10 | 10 |
| XO—HPX | 70 | 288 | 797 | 554 |
| XO—HPX—SOD | 12 | 22 | 48 | 60 |
| $H_2O_2$ | 10 | 11 | 11 | 11 |
| ascorbic acid | 10 | 11 | 11 | 11 |
| 1,4-hydroquinone | 10 | 11 | 10 | 11 |
| propylamine | 10 | 10 | 10 | 10 |
| diethylamine | 11 | 10 | 10 | 11 |
| glucose | 10 | 10 | 10 | 10 |
| esterase | 17 | 20 | 23 | 15 |

(* numeric values in Table 1 above are relative fluorescence intensity values obtained by calculating based on the assumption that the fluorescence response intensity of the blank test was 10.)

[2. Quantitativity]

According to a 96 wellmicroplate assay, sensitivity and quantitativity of the fluorescence response of the probe (the compound 1d) in the HPX/XO system were tested. Specifically, a DMSO solution of 1d (10 mM) was diluted by 400-fold with HEPES (pH 7.4, 10 mM) so as to prepare a probe solution, and this probe solution (150 μL) was mixed with a HEPES solution of HPX (10 μL) and a HEPES solution of XO (0.26 U/mL, 10 μL), and was allowed to stand still at 37° C. for 10 minutes, and thereafter, a fluorescence intensity was measured. Herein, by conducting the measurement with various concentrations of HPX, it was found that a detection limit value of the concentration of HPX was 5.0 pmol (RSD, n=8; 2.7%), and the value was acceptable for detection at a cellular level. Moreover, from the result that a favorable linear calibration curve was obtained with the concentration of HPX ranging from the detection limit value to 10.0 nmol, it was found that the fluorescence response of 1d showed favorable reliability with respect to an amount of $O_2^{-\bullet}$ generated by the enzyme reaction between HPX and XO. A correlation coefficient of this linear calibration curve was 1.000, and an inclination thereof was 0.58 au/pmol.

Furthermore, the quantitativity was tested in the same manner as the above-described measurement, except using a different apparatus for measuring a fluorescence intensity and setting a different assay condition, then it was found that excellent quantitativity was shown as well. More specifically, an assay condition was the same as that in the above-described measurement, except providing a DMSO solution of 1d with a concentration of 5 mM, preparing a probe solution by diluting this DMSO solution by 400-fold with HEPES (pH 7.4, 10 mM), and using 180 μL of the probe solution. Fluorescence intensity measurement was conducted by using an ETC-272 Peltier thermostatted single cell holder (trade name) manufactured by JASCO Corporation or a SpectraMax GeminiEM fluorescence plate reader (trade name) manufactured by Molecular Devices Corporation provided with a FP-750 spectrofluorometer (trade name) manufactured by JASCO Corporation. As a result, a detection limit value of the concentration of HPX was 1.0 pmol (RSD, n=8; 2.9%), and a favorable linear calibration curve with a correlation coefficient of 0.9993 and an inclination of 0.80 au/pmol was obtained, with the concentration of HPX ranging from the detection limit value to 2.0 nmol. The inclination of this linear calibration curve is different from that of the above-described measurement, because of using the arbitrary units for the fluorescence intensities and the different measurement apparatuses.

[3. Application to Cell System]

It is known that, if neutrophils are stimulated by phorbol ester, superoxide is produced. A capability of 1d as a fluorescent probe for measuring this phenomenon was tested by using neutrophils that were stimulated by phorbol myristate acetate (PMA), then it became clear that 1d could detect superoxide with high sensitivity in a cell system also. A specific testing method will be described below.

Firstly, whole blood donated by a good-health volunteer was heparinized, and it was subjected to centrifugal separation after adding a Mono-Poly resolving medium manufactured by Dainippon Pharmaceutical Co. Ltd. thereto. After the separation, cells were washed with PBS (−) twice, were suspended again at a concentration of $1.0 \times 10^6$ or $1.0 \times 10^5$ cells/mL by using PBS (+), and were maintained under an ice-cold condition until they were used. Herein, PBS denotes phosphate buffered saline, PBS (+) denotes PBS containing $CaCl_2$ of 0.54 mM and $MgSO_4$ of 1.22 mM, and PBS (−) denotes PBS containing none of them. The thus obtained cell suspension (100 μL), a probe solution (25 μM in PBS (+), 50 μL), and a PMA solution (0.64 μM in PBS (+), 50 μL) or a blank solution (PBS (+), 50 μL) were added into a 96-well flat-bottomed titer plate (manufactured by ASAHI TECHNO GLASS CORPORATION). Fluorescence intensity measurement was conducted immediately (measurement at the time 0), and thereafter, incubation was conducted at 37° C. for 120 minutes. During the incubation, a change of the fluorescence intensity of the cells was measured once every 30 minutes. All of the measurements were conducted by using a CytoFluor II multiwell fluorescence plate reader (trade name) manufactured by PerSeptive Biosystems, Inc. in the U.S., by setting an excitation filter and an emission filter at 485±20 nm and 530±25 nm, respectively.

Figure 2:
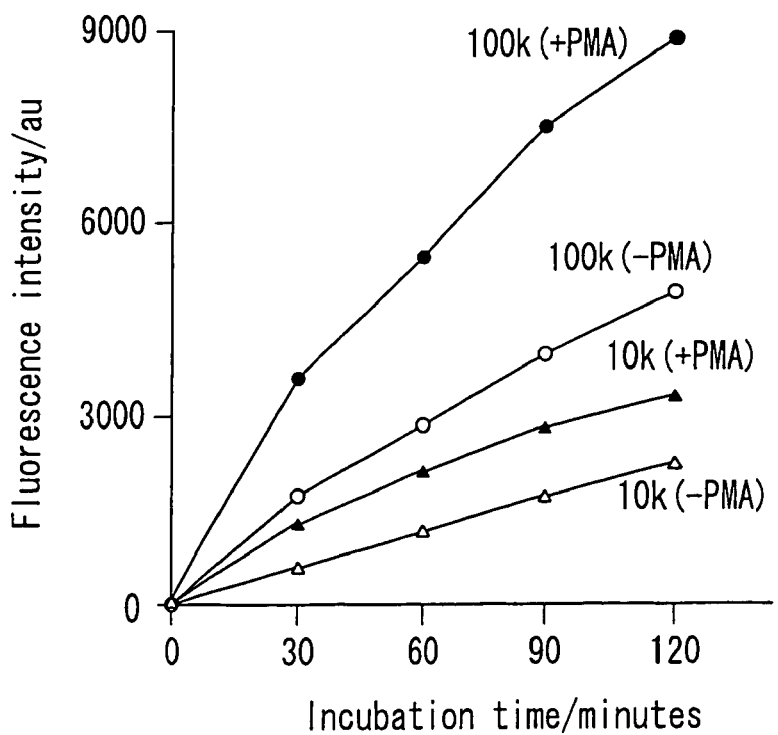
FIG. 2 is a graph showing results of tests in which the compound 1d is applied to a cell system.

The graph in FIG. 2 shows results of the above-described test. This figure shows the results obtained by conducting the test in the presence and absence of PMA, in the cases where the number of cells in each well was $1.0 \times 10^4$ and $1.0 \times 10^5$, respectively. A horizontal axis of the graph denotes an incubation time (minute), and a vertical axis thereof denotes a fluorescence intensity (au). As shown in the figure, an assay of the compound 1d clearly showed that PMA-stimulating neutrophils emitted $O_2^{-\bullet}$. An increase of the fluorescence intensity also was observed in unstimulated cells, but this increase is thought to be caused by activation of the neutrophils due to an interaction between a surface of an used tissue culture plate and the cells, according to the conventional studies.

Figure 3:
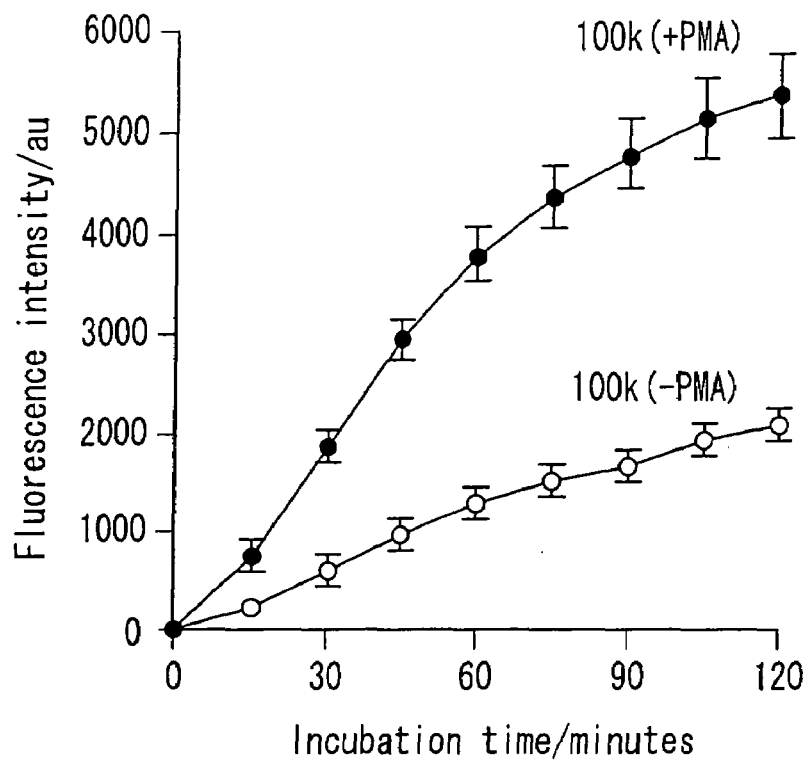
FIG. 3 is another graph showing the results of the tests in which the compound 1d is applied to the cell system.

In addition, another test was conducted in the same manner as that of the above-described test, except using a different fluorescence intensity measurement apparatus, which was an ETC-272 Peltier thermostatted single cell holder (trade name) manufactured by JASCO Corporation or a SpectraMax GeminiEM fluorescence plate reader (trade name) manufactured by Molecular Devices Corporation provided with a FP-750 spectrofluorometer (trade name) manufactured by JASCO Corporation, and measuring a change of the fluorescence intensity once every 15 minutes. Then, similar results were obtained. The graph in FIG. 3 shows the results. The number of cells in each well was $1.0 \times 10^5$, a horizontal axis of the graph denotes an incubation time (minute). A vertical axis thereof denotes a fluorescence intensity (au), which is represented by a mean value±a standard deviation of measurement values of eight wells. Numeric values of the fluorescence intensities shown in FIG. 2 and FIG. 3 are different, because the arbitrary units and the different measurement apparatuses were used.

Moreover, a toxicity of the compound 1d with respect to the neutrophils was evaluated by estimating cell viability by a trypan blue dyeing method. More specifically, the neutrophils ($1.0 \times 10^5$ cells) were incubated at 37° C. for 120 minutes in a glass test tube coated with human serum albumin, in the presence of both of the compound 1d (6.25 μM) and PMA (0.16 μM), in the presence of either of them, and in the absence of them, respectively. Then, cell viability after the incubation with respect to cell viability before the incubation was measured. As a result, in the absence of 1d and PMA, the cell viability after the incubation was 98% of the cell viability before the incubation. Whereas, in the presence of the compound 1d only, the cell viability after the incubation was 95%; in the presence of PMA only, the cell viability after the incubation was 93%; and in the presence of both of the compound 1d and PMA, the cell viability after the incubation was 97%. Therefore, it was found that almost none of the neutrophils died in all of these conditions. As mentioned above, it was recognized that not only PMA but also the compound 1d did not show any significant toxicity with respect to the neutrophils during the incubation of 120 minutes.

The above-described results also showed that reductive deprotecting from the compound 1d into 2d was induced by $O_2^{-\bullet}$ effectively, and accordingly, the compound 1d functioned as a new fluorescent probe for detecting $O_2^{-\bullet}$ that was emitted from the PMA-stimulating neutrophils, and did not damage the cells during the incubation. It can be expected that this probe and its homologues facilitate measurement of cell-derived $O_2^{-\bullet}$, and help to analyze dynamic functions of oxidative stresses that are produced by not only mitochondrion but also phagocytes and vascular cells.

[4. Tests for Other Compounds]

A capability of each of the compounds 1a to 1c, 5a and 6a that includes a 2,4-dinitrobenzenesulfonyl group as a superoxide-detecting fluorescent probe was tested similarly to the compound 1d, then it became clear that all of the compounds were deprotected by superoxide so as to be transformed into fluorochromes that respectively corresponded to them. Moreover, it was found that each of the compounds 3, 4a, 5b and 6b to which a 4-trifluoromethyl-2-nitrobenzenesulfonyl group was introduced instead of the 2,4-dinitrobenzenesulfonyl group, and the compound 4b to which a 4-nitrobenzenesulfonyl group was introduced also were deprotected by superoxide similarly so as to be transformed into fluorochromes, respectively. Thus, it is thought that each compound synthesized from a combination of: a phenolic colorant; and a 2,4-dinitrobenzenesulfonyl group, a 4-trifluoromethyl-2-nitrobenzenesulfonyl group or a 4-nitrobenzenesulfonyl group can be used as a superoxide-detecting fluorescent probe similarly. An example of the usage thereof will be shown in Scheme 8 below. Furthermore, it can be expected that a compound for a fluorescent probe having characteristics that are suitable for its application purpose can be designed and developed freely, by designing the compound of the present invention freely within the limitation defined by the general formula (I) and using the fluorescence mechanism developed by the inventors of the present invention, without being limited to the above-described combinations. Examples of the application purpose of the compound of the present invention are varied, including an application to a faintly coloring technique using superoxide.

Scheme 8

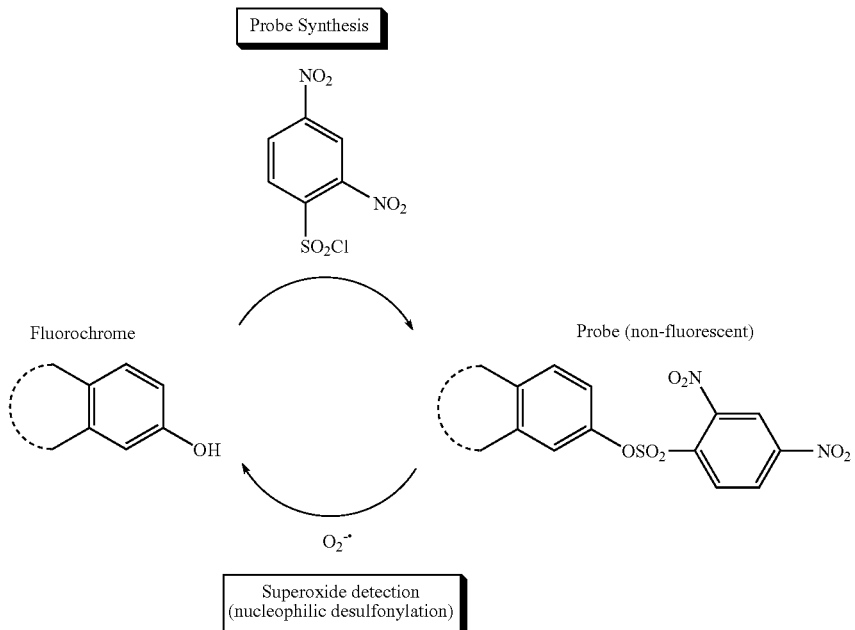

EXAMPLE 2

In the present example, in addition to the compound synthesized in Example 1, sulfonate compounds represented by the above formulae 4c to 4e, 7 and 8a to 8c were synthesized. And, the capability of each of these compounds as a mercapto compound-detecting fluorescent probe was tested. Fluorescence intensity measurement was conducted by using an ETC-272 Peltier thermostatted single cell holder (trade name) manufactured by JASCO Corporation or a SpectraMax GeminiEM fluorescence plate reader (trade name) manufactured by Molecular Devices Corporation provided with a FP-750 spectrofluorometer (trade name) manufactured by JASCO Corporation, unless otherwise stated. Other measurement conditions and the like were the same as those of Example 1.

[Synthesis of 4c]

Firstly, a suspension of tetrafluorofluorescein (2.0 g) and 2-nitrobenzenesulfonyl chloride (1.1 eq) in dichloromethane (20 mL) was prepared. Next, the temperature of this suspension was decreased to 0° C., and 2,6-lutidine (1.1 eq) was added to the suspension at this temperature. The obtained mixed solution was stirred at room temperature for 4 hours. The reaction solution was diluted with dichloromethane (200 mL), was washed with 1M hydrochloric acid (200 mL) and saturated saline (200 mL), and was dried over magnesium sulfate. Furthermore, the residue obtained by evaporating the solvent under a reduced pressure was refined by silica gel column-chromatography (dichloromethane-acetone=20:1), thereby obtaining the objective compound 4c. A yield and instrumental analytical values of this compound will be described below.

4c: 0.66 g (22%) as a dark yellow crystal. m.p. 234-246° C. (from AcOEt-hexane). $^1$H-NMR (270 MHz, [D]$_6$DMSO, TMS): δ=11.33 (s, 1H, COOH), 8.27 (t, $^3J_{H,H}$=8.9 Hz, 2H; aromatic), 8.17 (t, $^3J_{H,H}$=7.7 Hz, 1H; aromatic), 8.05-7.97 (m, 2H; aromatic), 7.85-7.73 (m, 2H; aromatic), 7.43 (d, $^3J_{H,H}$=7.4 Hz, 1H; aromatic), 7.02 (d, $^3J_{H,F}$=10.1 Hz, 1H; aromatic), 6.59 (d, $^3J_{H,F}$=10.9 Hz, 2H; aromatic). FTIR (KBr): ν=3254 (OH, br), 1752 (CO, s), 1553 (NO$_2$, s) cm$^{-1}$. FAB HRMS calcd for $C_{26}H_{12}F_4NO_9S$ (MH$^+$): 590.0169; found: 590.0167.

[Syntheses of 4d and 4e]

The compound 4d was obtained in the same manner as the synthesis of 4c, except using 2-nitro-4-methoxybenzenesulfonyl chloride instead of using 2-nitrobenzenesulfonyl chloride. Moreover, 4e was obtained in the same manner as the synthesis of 4c, except using 4-nitro-2-methoxybenzenesulfonyl chloride instead of using 2-nitrobenzenesulfonyl chloride. Yields and instrumental analytical values of these compounds will be described below.

4d: 0.46 g (15%) as dark orange powder. m.p. 111-125° C. $^1$H-NMR (270 MHz, CDCl$_3$, TMS): δ=8.07-8.01 (m, 2H; aromatic), 7.79-7.68 (m, 2H; aromatic), 7.36 (s, 2H; OH and aromatic), 7.20-7.16 (m, 2H; aromatic), 6.41 (dd, $^3J_{H,F}$=9.5, $^3J_{H,H}$=2.2 Hz, 1H; aromatic), 6.34 (dd, $^3J_{H,F}$=10.2 Hz, $^4J_{H,F}$=2.0 Hz, 1H; aromatic), 3.99 (s, 3H; OCH$_3$). FTIR (KBr): ν=3227 (OH, br), 1755 (CO, s), 1552 (NO$_2$, s) cm$^{-1}$. Elemental analysis (%) calcd for $C_{26}H_{11}F_4NO_9S$: C, 52.98; H, 1.88; N, 2.38; found: C, 53.01; H, 2.15; N, 2.23. FAB HRMS calcd for $C_{27}H_{14}F_4NO_{10}S$ (MH$^+$): 620.0275; found: 620.0280.

4e: 0.52 g (17%) as dark orange powder. m.p. 127-144° C. $^1$H-NMR (270 MHz, CDCl$_3$, TMS): δ=8.10-8.05 (m, 2H; aromatic), 7.95-7.90 (m, 2H; aromatic), 7.79-7.68 (m, 2H; aromatic), 7.18 (d, $^3J_{H,H}$=6.9 Hz, 1H; aromatic), 6.39 (dd, $^3J_{H,F}$=9.6, $^3J_{H,H}$=2.0 Hz, 1H; aromatic), 6.33 (dd, $^3J_{H,F}$=10.3 Hz, $^4J_{H,F}$=1.9 Hz, 1H; aromatic), 4.12 (s, 3H; OCH$_3$). FTIR (KBr): ν=3222 (OH, br), 1763 (CO, s), 1538 (NO$_2$, s) cm$^{-1}$. FAB HRMS calcd for $C_{27}H_{14}F_4NO_{10}S$ (MH$^+$): 620.0275; found: 620.0280.

[Synthesis of 7]

Firstly, a suspension of 4-methyl-7-hydroxycoumarin (1.0 g) in dichloromethane (20 mL) was prepared, and the temperature thereof was decreased to 0° C. At this temperature, triethylamine (1.2 eq) was added to the suspension. After it was stirred for 5 minutes, 2,4-dinitrobenzenesulfonyl chloride (1.2 eq) further was added thereto. The obtained mixed solution was stirred at room temperature for 4 to 6 hours. The reaction solution was diluted with dichloromethane (200 mL), was washed with 1M hydrochloric acid (200 mL) and saturated saline (200 mL), and was dried over magnesium sulfate. The residue obtained by evaporating the solvent under a reduced pressure was refined by silica gel column-chromatography (dichloromethane-acetone=20:1), thereby obtaining the objective compound 7. A yield and instrumental analytical values of this compound will be described below.

7: 2.2 g (95%) as white needles. m.p. 188-190° C. (from benzene). $^1$H-NMR (270 MHz, CDCl$_3$, TMS): δ=8.75 (d, $^4J_{H,H}$=2.0 Hz, 1H; aromatic), 8.45 (dd, $^3J_{H,H}$=8.6 Hz, $^4J_{H,H}$=2.0 Hz, 1H; aromatic), 8.16 (d, $^3J_{H,H}$=8.6 Hz, 1H; aromatic), 7.75 (d, $^3J_{H,H}$=8.6 Hz, 1H; aromatic), 7.21-7.16 (m, 2H; aromatic), 6.31 (s, 1H; aromatic), 2.41 (S, 3H; CH$_3$). FTIR (KBr): ν=1732 (CO, s), 1560 (NO$_2$, s), 1537 (NO$_2$, s) cm$^{-1}$. FAB HRMS calcd for $C_{16}H_{11}N_2O_9S$ (MH$^+$): 407.0185; found: 407.0184.

[Syntheses of 8a to 8c]

Each of the compounds 8a to 8c was synthesized in the same manner as the synthesis of 7, except using a derivative of fluorescein (1.0 g) that corresponded to each of structures of 8a to 8c, instead of using 4-methyl-7-hydroxycoumarin. Yields and instrumental analytical values of these compounds will be described below.

8a: 0.63 g (37%) as a yellow solid. m.p. 125-147° C. $^1$H-NMR (270 MHz, CD$_3$OD, TMS): δ 8.87 (d, $^4J_{H,H}$=2.8 Hz, 1H; aromatic), 8.44 (dd, $^3J_{H,H}$=9.2 Hz, $^4J_{H,H}$=2.8 Hz, 1H; aromatic), 8.03-7.98 (m, 1H; aromatic), 7.81-7.69 (m, 2H; aromatic), 7.33-7.16 (m, 3H; aromatic), 6.90-6.81 (m, 2H; aromatic), 6.69-6.55 (m, 3H; aromatic). FTIR (KBr): ν=3438 (OH, br) 1736 (CO, s), 1539 (NO$_2$, s) cm$^{-1}$. FAB HRMS calcd for $C_{26}H_{15}N_2O_{11}S$ (MH$^+$): 563.0397; found: 563.0396.

8b: 0.75 g (46%) as a yellow solid. m.p. 131-156° C. $^1$H-NMR (270 MHz, CDCl$_3$, TMS): δ 8.70 (s, 1H; aromatic), 8.58 (d, $^3J_{H,H}$=8.4 Hz, 1H; aromatic), 8.32 (d, $^3J_{H,H}$=8.4 Hz, 1H, aromatic), 8.06 (d, $^3J_{H,H}$=6.8 Hz, 1H; aromatic), 7.71-7.66 (m, 2H; aromatic), 7.15 (d, $^3J_{H,H}$=6.8 Hz, 1H; aromatic), 7.05 (s, 1H; aromatic), 6.66 (s, 1H; aromatic), 6.63 (s, 1H; aromatic), 6.47 (s, 1H; aromatic), 5.67 (s, 1H; OH), 2.06 (S, 6H; CH$_3$×2). FTIR (KBr): ν=3318 (OH, br), 1735 (CO, s), 1557 (NO$_2$, s), 1542 (NO$_2$, s) cm$^{-1}$. FAB HRMS calcd for $C_{28}H_{19}N_2O_{11}S$ (MH$^+$): 590.0710; found: 599.0698.

8c: 0.62 g (38%) as a yellow solid. m.p. 143-158° C. (from CHCl$_3$). $^1$H-NMR (270 MHz, CDCl$_3$, TMS): δ 8.67 (d, $^4J_{H,H}$=2.1 Hz, 1H; aromatic), 8.55 (dd, $^3J_{H,H}$=8.6 Hz, $^4J_{H,H}$=2.1 Hz, 1H; aromatic), 8.25 (d, $^3J_{H,H}$=8.6 Hz, 1H, aromatic), 8.01 (d, $^3J_{H,H}$=7.1 Hz, 1H; aromatic), 7.72-7.60 (m, 2H; aromatic), 7.16 (d, $^3J_{H,H}$=7.4 Hz, 1H; aromatic), 6.73 (d, $^3J_{H,H}$=7.4 Hz, 1H; aromatic), 6.60 (d, $^3J_{H,H}$=8.7 Hz, 1H; aromatic), 6.55 (d, $^3J_{H,H}$=8.7 Hz, 1H; aromatic), 6.48 (d, $^3J_{H,H}$=8.7 Hz, 1H; aromatic), 5.50 (s, 1H; OH), 2.44 (S, 3H; CH$_3$), 2.38 (S, 3H; CH$_3$). FTIR (KBr): ν=3266 (OH, br), 1735 (CO, s), 1558 (NO$_2$, s), 1541 (NO$_2$, s) cm$^{-1}$. FAB HRMS calcd for $C_{28}H_{19}N_2O_{11}S$ (MH$^+$): 590.0710; found: 599.0705.

(Evaluation as Mercapto Compound-Responsive-Type Fluorescent Probe)

[1. Specificity with Respect to Mercapto Compound]

Figure 4:
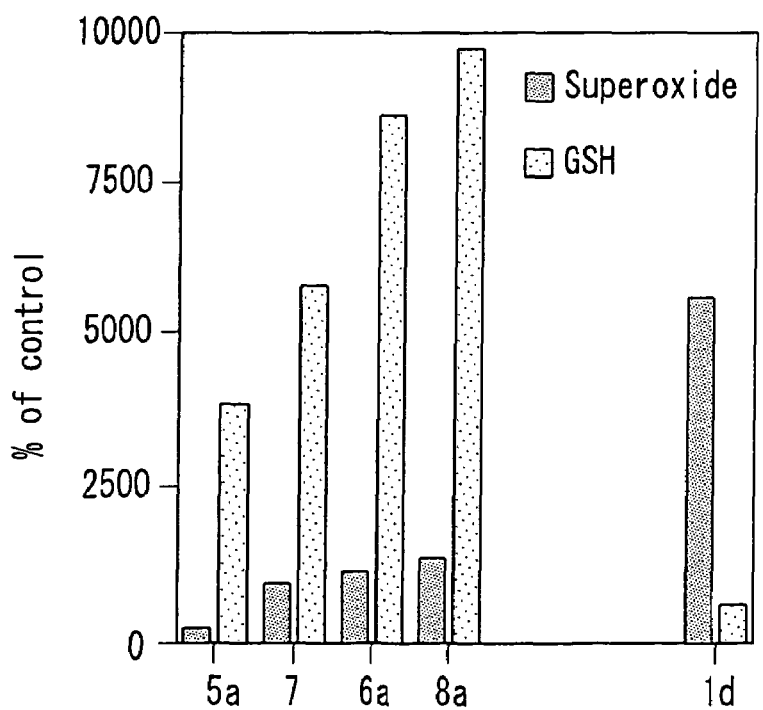
FIG. 4 is a graph showing specificity of respective compounds 5a, 7, 6a, 8a and 1d with respect to superoxide or glutathione.

The reactivity of each of the compounds 1d, 5a, 6a, 7 and 8a with respect to superoxide and glutathione (GSH) that is a kind of thiol was tested under the same conditions as those of [1-3. Superoxide-selectivity (2)] in Example 1. FIG. 4 shows results thereof. A vertical axis thereof denotes a fluorescence intensity, which is represented in % of control. As shown in the figure, it was found that 1d had excellent superoxide-selectivity (specificity), and 5a, 6a, 7 and 8a had excellent mercapto compound-selectivity, besides showing responses with respect to superoxide as well. Moreover, it was recognized that the compounds 8b and 8c also responded to glutathione with high sensitivity. From these results, it is thought that 7-hydroxycoumarin, resorufin, fluorescein and O-2,4-dinitrobenzenesulfonylates that are their derivatives, which respectively are fluorescent compounds having phenolic hydroxyl groups, particularly preferably are used as probes that respond to mercapto compounds such as glutathione and cysteine in a short period of time with high sensitivity. Furthermore, responses of 5a, 6a, 7, 8a, 8b and 8c with respect to the each of the compounds listed in Table 1 above in ([1-3. Superoxide-selectivity (2)] in Example 1) were tested under the same conditions as those of Example 1, but almost no response was shown. Thus, from the results that the compounds 5a, 6a, 7, 8a, 8b and 8c hardly responded to other reactants except mercapto compounds, such as $H_2O_2$, amines and the like, it was found that the selectivity of these compounds with respect to a mercapto compound were exceedingly high.

[2. Evaluation as Mercapto Compound-Responsive-Type Fluorescent Probe]

Next, a capability of each of the compounds 6a and 8a as a mercapto compound-responsive-type fluorescent probe was evaluated.

Quantitativity and the like of each of the compounds 6a and 8a with respect to a mercapto compound were evaluated, by using glutathione (GSH) and cysteine that are kinds of thiol. More specifically, an EtOH solution of the compound 6a (10 mM) was prepared, and it further was diluted by 500-fold with a HEPES buffer solution having a pH of 7.4, thereby preparing a probe solution containing the compound 6a. Next, 200 μL of this probe solution and 10 μL of each of solutions of glutathione or cysteine (dissolved in a HEPES buffer solution having a pH of 7.4) with various concentrations were added into each well of a 96-wellmicroplate, and were allowed to stand still at 37° C. for 10 minutes so as to undergo a reaction. Moreover, a probe solution containing 8a was prepared in the same manner as the preparation of the solution of the compound 6a except using 8a instead of 6a, and this probe solution also was allowed to react with a thiol solution in the same manner as the reaction of the probe solution containing 6a. Then, a fluorescence response of each well was measured after the reaction. The measurement of 6a was conducted at $\lambda_{ex}$=383 nm and $\lambda_{em}$=500 nm, and the measurement of 8a was conducted at $\lambda_{ex}$=483 nm and $\lambda_{em}$=515 nm. Herein, $\lambda_{ex}$ denotes an excitation wavelength, and $\lambda_{em}$ denotes an emission wavelength.

Figure 5A:
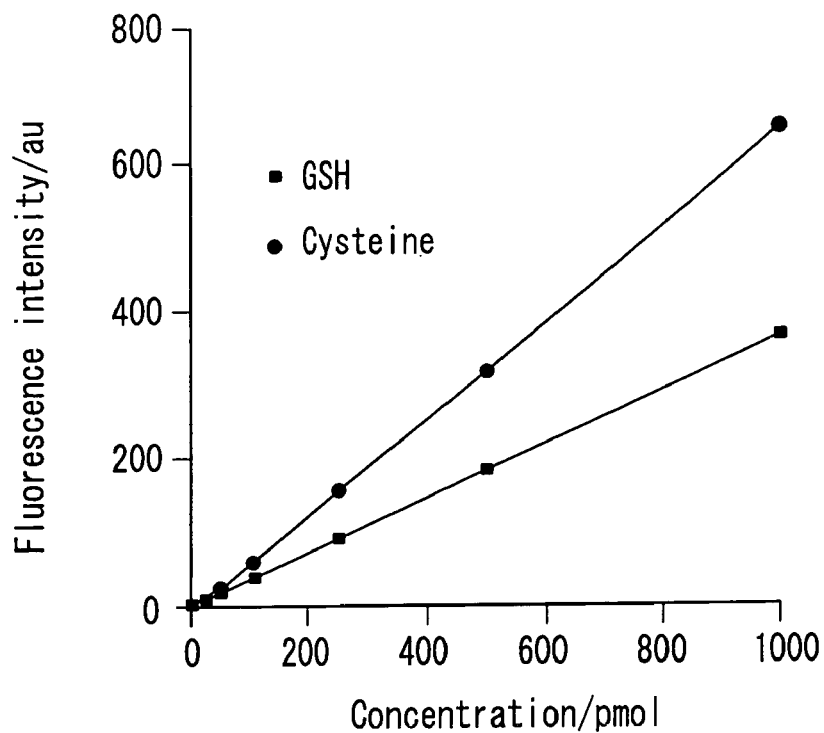
Figure 5B:
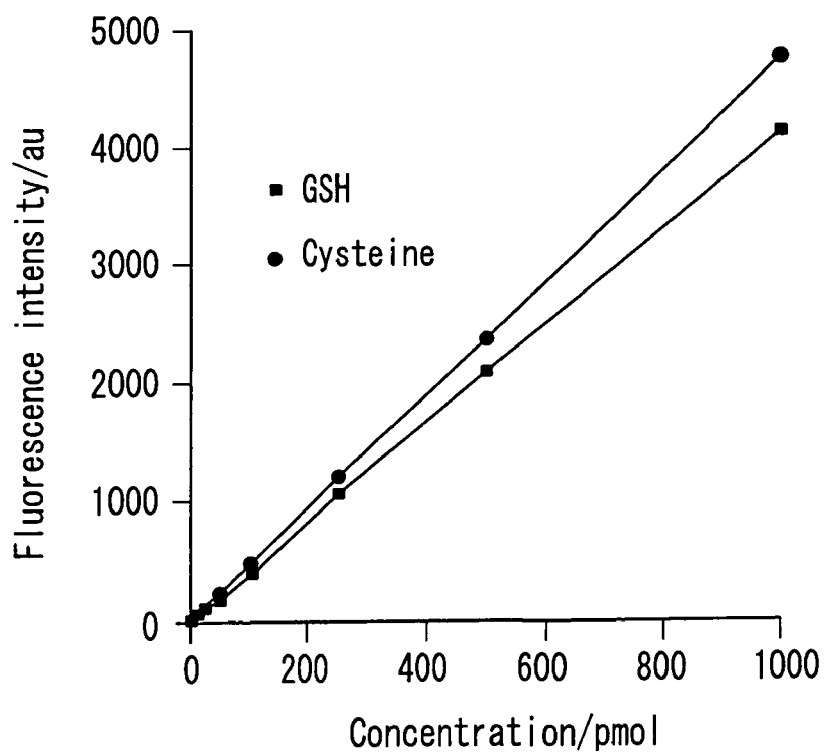

FIG. 5 shows measurement results of the above-described fluorescence responses. FIG. 5A is a graph showing the measurement result of 6a, and FIG. 5B is a graph showing the measurement result of 8a. As shown in the figures, in the case of using 6a, both of detection limits of GSH and cysteine were 7 pmol, and a favorable calibration curve was obtained in a concentration range from 7 pmol to 1000 pmol. Herein, in the case of GSH, an inclination of its calibration curve was 0.37 au/pmol and a correlation coefficient (r) thereof was 0.9998, and in the case of cysteine, an inclination of its calibration curve was 0.66 au/pmol and a correlation coefficient (r) thereof was 0.9995. Whereas, in the case of using 8a, detection limits of GSH and cysteine were 2 pmol and 1 pmol respectively, and a favorable calibration curve of each of GSH and cysteine was obtained in a concentration range from the detection limit to 1000 pmol. Herein, in the case of GSH, an inclination of the calibration curve was 4.25 au/pmol and a correlation coefficient (r) thereof was 1.0000, and in the case of cysteine, an inclination of the calibration curve was 4.82 au/pmol and a correlation coefficient (r) thereof was 0.9999.

From these results, it was shown that 6a and 8a can be used as mercapto compound-responsive-type fluorescent probes. More specifically, it was found that, from the values of the correlation coefficients (r), 6a and 8a had excellent quantitativity, and from the magnitude of their inclinations, they had high sensitivity. In particular, 8a had high sensitivity.

Moreover, a fluorescent probe including 6a or 8a had characteristics of having a very short reaction time and requiring any process for separating the reagent before and after the reaction, because none of 6a or 8a itself had fluorescence and only a colorant produced by the reaction had fluorescence.

Furthermore, the fluorescent probe including 6a or 8a mentioned above was allowed to react in the same conditions except using other nucleophilic agent including a hydroxyl group, an amino group and the like, instead of using thiol, then it was recognized that the fluorescent probe showed no fluorescence at all. Accordingly, it was found that these fluorescent probes did not respond to a hydroxyl group, an amino group or the like, and had high specificity (selectivity) with respect to a mercapto compound.

In addition, similar test was conducted with respect to the compounds 5a, 7, 8b and 8c, and similar results were obtained.

[3. Acetyl Cholinesterase Assay]

As shown in Scheme 9 below, by an enzyme reaction between acetyl choline as a substrate and acetyl cholinesterase as an enzyme, thiocholine that is a kind of a mercapto compound (thiol) is generated. It can be expected that, by detecting this thiocholine by the sulfonate compound of the present invention, for example, as shown in Scheme 10 below, an activity of acetyl cholinesterase (AChE) can be measured in a short period of time. Herein, Scheme 10 is only an example of a presumed mechanism, and does not limit the present invention.

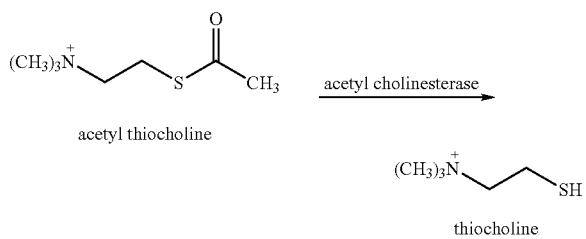

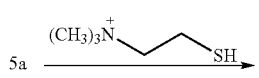

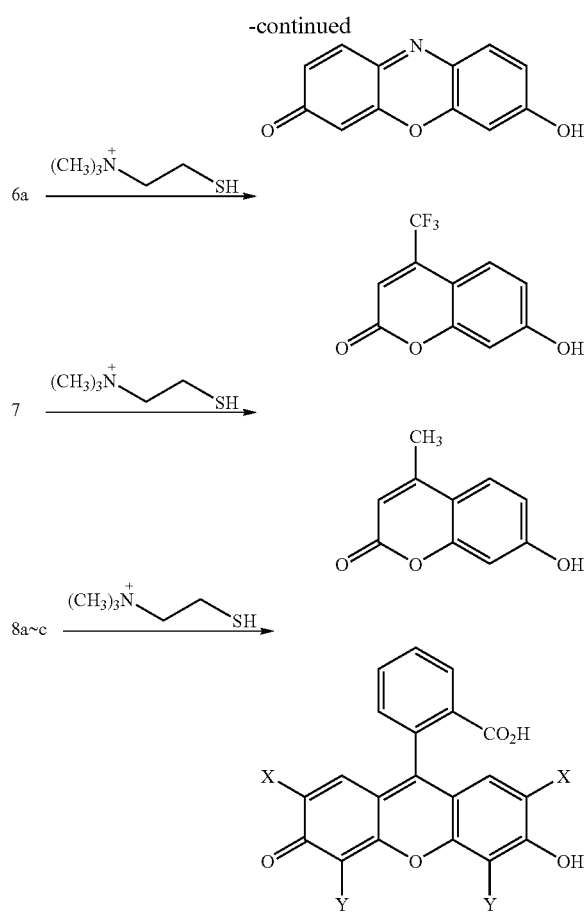

The inventors of the present invention confirmed that each of the above-described compounds actually can be used for the measurement of the activity of acetyl cholinesterase. Specific operational processes of the measurement using the compound 8a will be shown below. Firstly, an EtOH solution of the compound 8a (10 mM) was prepared, and it further was diluted by 500-fold with a HEPES buffer solution having a pH of 7.4, thereby preparing a probe solution containing the compound 8a (20 μM). Whereas, a solution (1 mM) was prepared by dissolving commercially available acetyl thiocholine in a HEPES buffer solution having a pH of 7.4. Moreover, acetyl cholinesterase (AChE) solutions (solutions obtained by dissolving acetyl cholinesterase in a HEPES buffer solution having a pH of 7.4) with various concentrations (activity levels) were prepared.

Figure 6:
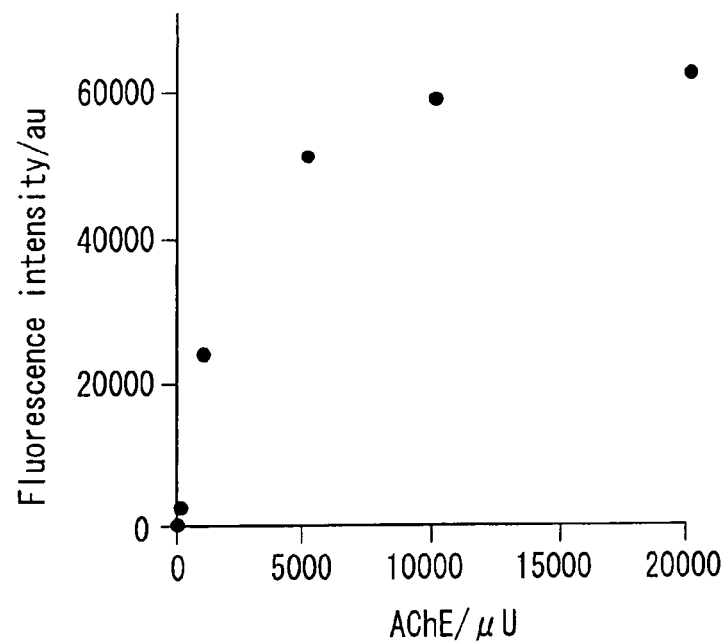

Next, 200 μL of the probe solution, 10 μL of the acetyl thiocholine solution and 10 μL of each of the acetyl cholinesterase (AChE) solutions with various concentrations (activity levels) were added into each well of a 96-wellmicroplate, and underwent an enzyme reaction at 37° C. for 10 minutes. Immediately after the reaction, a fluorescence response of each well was measured at $\lambda_{ex}$ (excitation wavelength) of 483 nm and $\lambda_{em}$ (emission wavelength) of 515 nm. FIG. 6 shows measurement results of the fluorescence responses. In the figure, a horizontal axis denotes an activity level of AChE (μU), and a vertical axis denotes a fluorescence intensity (au). As shown in the figure, the fluorescence response obtained with respect to each well showed favorable reliability to the activity level of AChE. Moreover, in a range from 0.1 μU to 0.5 μU, a favorable linear relationship was observed between the AChE activity and the fluorescence response (inclination=28.8 au/μU, r=0.9998). The AChE assay had characteristics including not only excellent sensitivity due to a small background response, but also an exceedingly short reaction time of 10 minutes.

Figure 7:
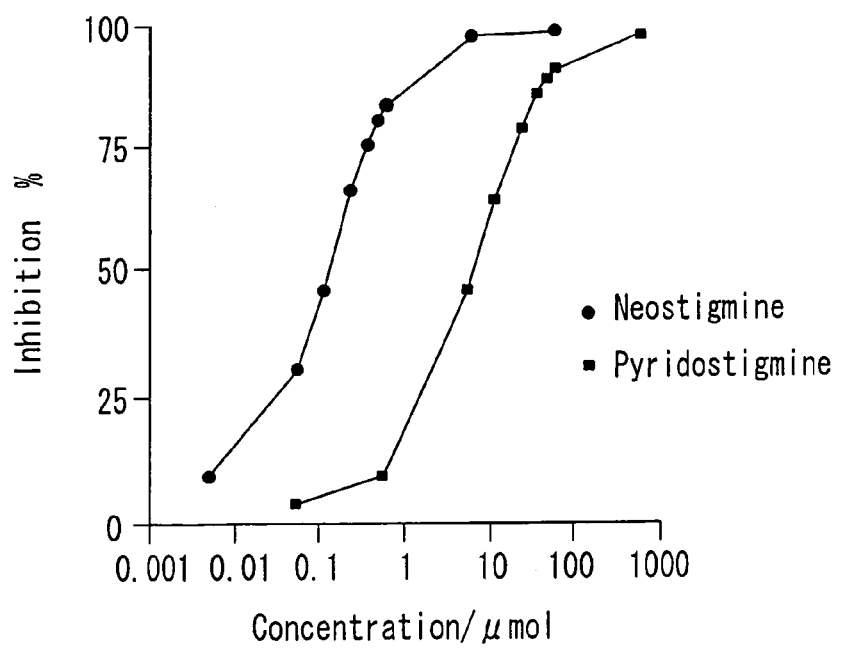

Moreover, it was confirmed that the above-described assay method also can be used for measuring an activity of an AChE inhibitor, by using neostigmine and pyridostigmine that are well-known anticholinergic agents. Specific operational processes thereof will be described below. Firstly, a probe solution containing 8a, an acetyl thiocholine solution and an acetyl cholinesterase (AChE) solution were prepared in the same manner as described above. However, a concentration (activity level) of the AChE solution was fixed to be 5 U/mL. Whereas, neostigmine solutions and pyridostigmine solutions with various concentrations (each of them was dissolved in a HEPES buffer solution having a pH of 7.4) were prepared. Then, this probe solution (25 μM, 150 μL), the acetyl thiocholine solution (1 mM, 10 μL), the AChE solution (5 U/mL, 10 μL) and each of the neostigmine solutions or the pyridostigmine solutions with various concentrations were added into each well of a 96-wellmicroplate, and underwent an enzyme reaction at 37° C. for 10 minutes, and thereafter, a fluorescent response of each well was measured. Each measurement was conducted at $\lambda_{ex}$ (excitation wavelength) of 483 nm and $\lambda_{em}$ (emission wavelength) of 515 nm. Then, inhibition % values were calculated from fluorescence intensities, thereby forming an inhibitory activity curve. FIG. 7 shows the inhibitory activity curve. A horizontal axis thereof denotes a concentration of neostigmine or pyridostigmine (μmol), and a vertical axis thereof denotes the inhibition % value caluculated from the fluorescence intensity.

$IC_{50}$ values of neostigmine and pyridostigmine estimated from the inhibitory activity curve in FIG. 7 were 0.18 μM and 0.29 μM, respectively. These values did not correspond to literature values known as $IC_{50}$ values of neostigmine and pyridostigmine, which was caused by different measurement conditions and the like. However, a relative difference in degree between the $IC_{50}$ values of both of these anticholinergic agents showed a favorable correlation with that of the literature values. Thus, it was found that the compound 8a can be used as an activity measurement agent that has high accuracy with respect to the AChE inhibitor.

An AChE assay and measurement of AChE inhibitory activities are very important for diagnoses of diseases related to AChE, for example, an Alzheimer's disease, and for screening of candidate compounds for new pharmaceuticals. In particular, an AChE inhibitor recently has received attention as a therapeutic agent for an Alzheimer's disease, and it can be expected that the sulfonate compound of the present invention is significantly useful for screening an AChE inhibitor, according to the above-described test results.

[4. Application as Thiophosphonate Group-Responsive-Type Probe]

Moreover, a capability of the sulfonate compound of the present invention as a fluorescent probe for mercapto compounds other than thiol (a compound in which a —SH group is bonded to a carbon atom) was examined. More specifically, it became clear that the compounds 5a, 6a, 7 and 8a to 8c also responded to a thiol group in a so-called thiophosphonate group that is included in adenosine 5'-[γ-thio]triphosphate (γ-S-ATP) and adenosine monothiophosphate (S-AMP). Test results obtained by using the compounds 8a to 8c and γ-S-ATP will be described below.

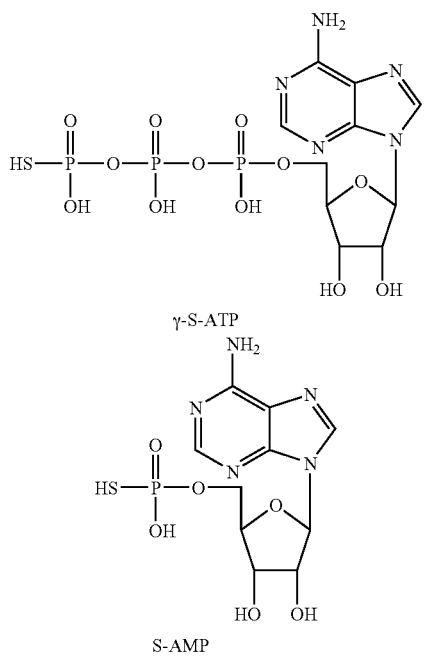

γ-S-ATP

S-AMP

Figure 8:
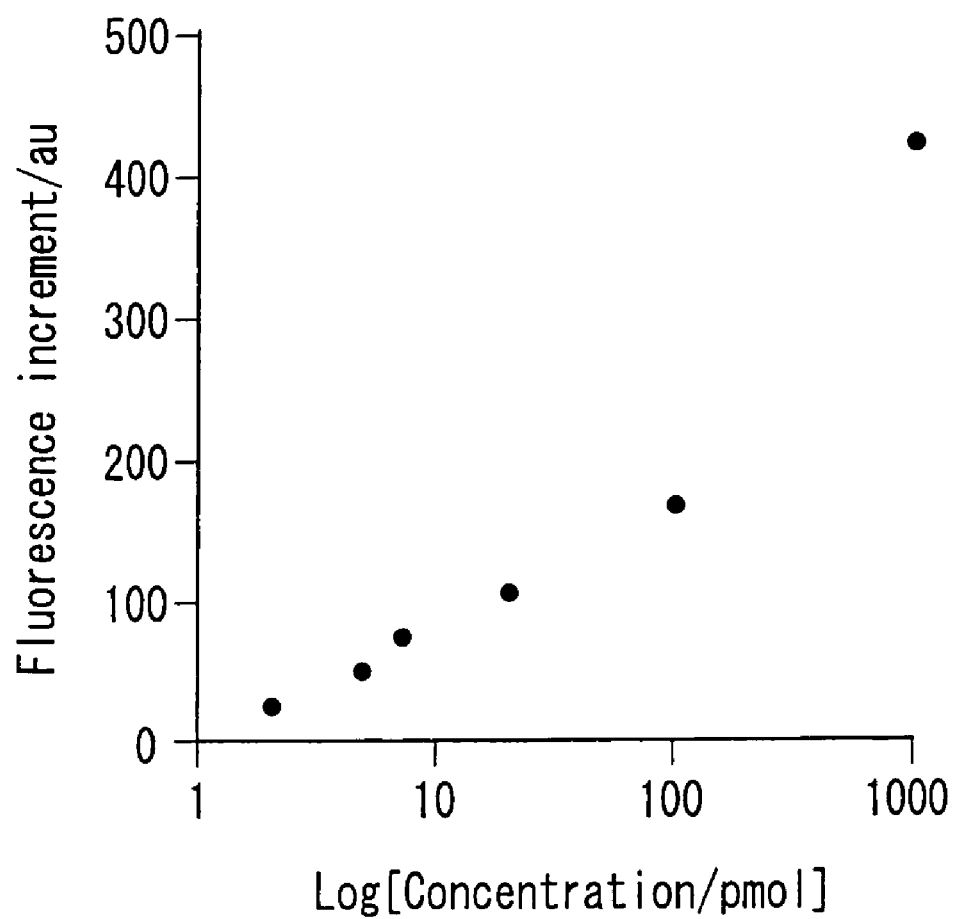
FIG. 8 is a graph showing a fluorescence response of the compound 8a with respect to γ-S-ATP.

A solution of 8a (20 μM, 200 μL) and each of solutions of γ-S-ATP with various concentrations (each of them was a solution obtained by dissolving γ-S-ATP in an imidazole buffer solution having a pH of 7.4) were added into each well of a 96-wellmicroplate, and were allowed to react at 37° C. for 180 minutes, and thereafter, a fluorescence response of each well was measured. The measurement was conducted at $\lambda_{ex}$ (excitation wavelength) of 483 nm and $\lambda_{em}$ (emission wavelength) of 515 nm. FIG. 8 shows results thereof. As shown in the figure, the response observed after the reaction showed favorable reliability to the concentration of γ-S-ATP. In addition, a detection limit was 5 pmol, which showed that 8a had high sensitivity with respect to γ-S-ATP. Moreover, similar tests were conducted with respect to 8b and 8c, and then it also became clear that these compounds could detect γ-S-ATP with sensitivity still higher than that of 8a.

As mentioned above, from the results that 8a to 8c showed responses with respect to a thiophosphonate group, it can be expected that a kinase assay can be structured based on mechanisms represented by Schemes 11 and 12 below, by using these compounds for mercapto compound-responsive-type fluorescent probes. By actually using the compound 8a, fluorescence responses of 8a with respect to thiophosphorylated protein (provided by SYSMEX CORPORATION) having different introduction degrees of the thiophosphonate group was measured, then the fluorescence responses corresponding to the respective introduction degrees were obtained.

Scheme 11

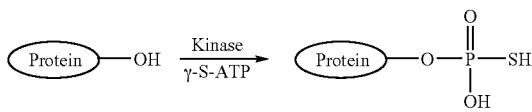

Scheme 12

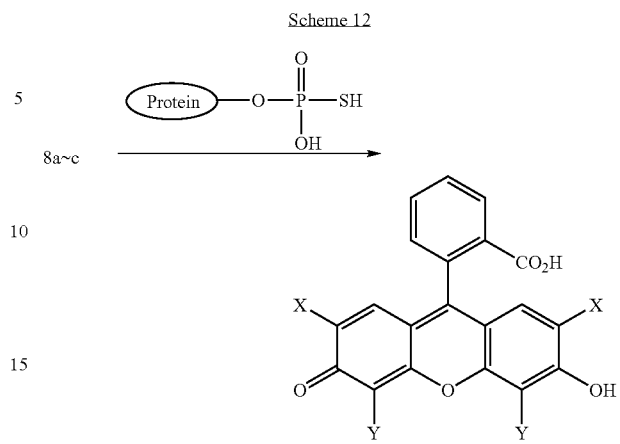

More specific description about Schemes 11 and 12 above will be provided below. Kinase is an enzyme for phosphorylating a hydroxyl group in a tyrosine residue or the like of protein in the presence of ATP, but if this enzyme reaction is effected by using γ-S-ATP instead of ATP, thiophosphorylated protein is produced. A kinase assay can be conducted by detecting this thiophosphorylated protein by using a thiol-responsive-type fluorescent probe. It is thought that examples of an actual method for using this kinase assay for clinical diagnoses include the below-described two methods (1) and (2).

(1) A method using a microplate on which a specific substrate of kinase is fixed can be conducted by, for example, performing below-described steps (i) to (v) sequentially:

(i) separation of kinase as an object to be analyzed from a sample (blood or tissue) by using an antibody, that is, immunoprecipitation;

(ii) thiophosphorylation of the fixed substrate by the separated kinase and γ-S-ATP, that is, an enzyme reaction with kinase;

(iii) wash-out of the additives;

(iv) a fluorescence process by a reaction with the thiophosphonate group-responsive-type probe; and (v) detection by a fluorescent plate reader.

(2) A method for blotting the specific substrate of kinase can be conducted by, for example, performing below-described steps (i) to (v) sequentially:

(i) separation of kinase as an object to be analyzed from a sample (blood or tissue) by using an antibody, that is, immunoprecipitation;

(ii) thiophosphorylation of the substrate by the separated kinase and γ-S-ATP, that is, an enzyme reaction with kinase;

(iii) separation of the thiophosphorylated substrate and blotting thereof on a membrane;

(iv) a fluorescence process by a reaction with the thiophosphonate group-responsive-type probe; and (v) detection by a fluorescent image analyzer.

It is thought that, according to the above method (1) or (2), a certain kind of kinase can be detected with specificity from many kinds of kinase that are related to various physiological phenomena (differentiation, division and proliferation of cells, and cycles thereof, by using specific antibodies and substrates. Therefore, it can be expected that the thiophosphonate group-responsive-type probe can be used not only for a research reagent for measuring activity levels of kinase, but also for the application to clinical tests such as cancer diagnoses.

As described above, from the results of the present example, it was found that, according to the acetyl AChE assay and the kinase assay of the present invention, simple measurement can be conducted without using any radioisotope label that affects the environment More specifically, in the AChE assay, an enzyme reaction and a fluorescence reaction also can proceed at the same time, whereas, in the kinase assay, the measurement also can be conducted with simple operational process in which a fluorescence reaction proceeds after an enzyme reaction, and the measurement using only an enzyme substrate and a probe as a reagent can be conducted as well. Moreover, from the above-described results in the example, it is thought that detection sensitivity of the measurement method using the mercapto compound-detecting fluorescent probe of the present invention can be equivalent to that of chemiluminescence.

Furthermore, other methods for enzyme activity measurement by using the mercapto compound-detecting probe of the present invention can be structured easily, by molecular-designing them so that thiol may be produced from these enzyme substrates by enzyme reactions. An example thereof is Scheme 13 below. Considering these advantages, it can be expected that the mercapto compound-responsive-type fluorescent probe can be used as a reagent having various functions that are suitable for structuring various types of kits for enzyme assays.

Scheme 13

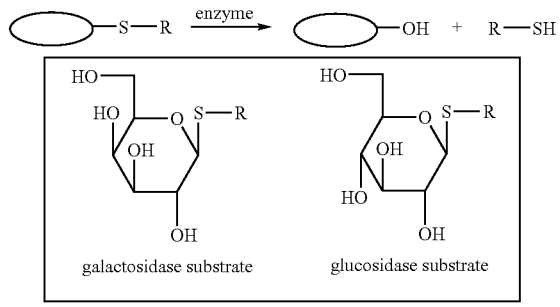

INDUSTRIAL APPLICABILITY

As described above, the sulfonate compound of the present invention can be used suitably for a fluorescent probe that responds to superoxide with high selectivity. Considering the importance of a fluorescent probe as a reagent for the current study of cytophysiology, and the recent significant development of image analyzing systems using fluorescence microscopes and flow cytometry (cell sorters) in the aspects of hardware and software, the demand for fluorescent probes further will be increased in the market in the future. The present invention can be used favorably for developing new treatment and seeds for new pharmaceuticals for diseases related to active oxygen species and acetyl cholinesterase, which are suitable for, for example, bio-imaging, clinical analyses and the like. In particular, it can be expected that the mercapto compound-detecting probe is in good use for screening therapeutic agents for an Alzheimer's disease, cancers and the like, through the detection of acetyl cholinesterase activities and the application to a kinase assay. Moreover, the application purpose of the sulfonate compound of the present invention is not limited to a fluorescent probe, and can be used for any purposes.

The invention claimed is:

1. A sulfonate compound represented by a formula (I) below,

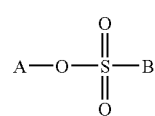

where, in the formula (I), an atomic group A-O is an atomic group that forms a fluorescent compound upon cleavage of a covalent bond between the atomic group A-O and a sulfonyl group, one or a plurality of atomic groups B—$SO_3$— are bonded to an atomic group A, B is benzene ring that is substituted by one or a plurality of electron-withdrawing groups, the electron-withdrawing group is at least one selected from the group consisting of an alkyl halide group (except a monochloroalkyl group, a monobromoalkyl group and a monoiodoalkyl group), a nitro group and a cyano group, and B may be the same or different in kind in the case where the plurality of B exist, the atomic group B is at least one selected from the group consisting of: a 2,4-dinitrophenyl group; a 2-nitro-(4-trifluoromethyl)phenyl group; a 2-nitro-4-methoxyphenyl group; a 4-nitro-2-methoxyphenyl group; a 2-nitro-4-methylphenyl group; a 4-nitro-2-methylphenyl group; a 2-nitro-4,6-dimethylphenyl group; a 4-nitro-2,6-dimethylphenyl group; a 2-nitro-4-chlorophenyl group; a 4-nitro-2-chlorophenyl group; and a 2-nitro-4-isopropylphenyl group, A is a formula represented by a formula (X-1) or (X-2) below,

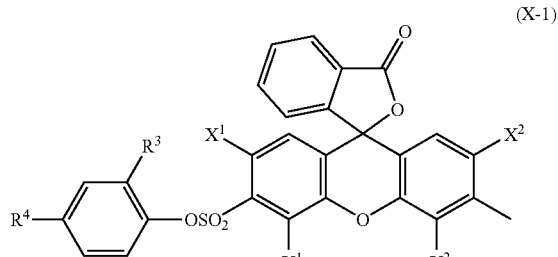

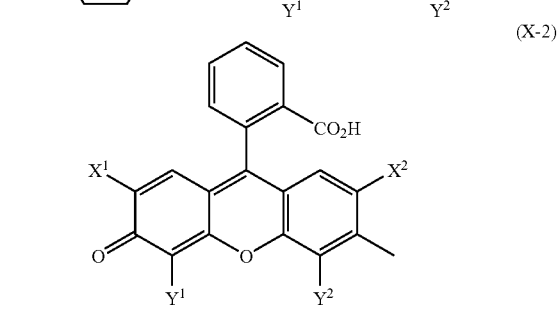

where, in the above formulae, each of $X^1$, $X^2$, $Y^1$ and $Y^2$ is hydrogen atom, a straight or branched alkyl group having 1 to 6 carbon atoms or a halogen, $X^1$, $X^2$, $Y^1$ and $Y^2$ may be the same or different, $R^3$ is a hydrogen atom, a nitro group, a methyl group, a chloro group or a methoxy group, and $R^4$ is a hydrogen atom, a nitro group, a trifluoromethyl group, a methyl group, an isopropyl group, a chloro group or a methoxy group, wherein a fluorescent compound formed upon cleavage of the covalent bond between the atomic group A-O and the sulfonyl group is at least one selected from the group consisting of: fluorescein and its derivatives.

2. The sulfonate compound according to claim 1, wherein the alkyl halide group is a perfuoroalkyl group.

3. The sulfonate compound according to claim 1, represented by any of formulae (i) and (ii) below,

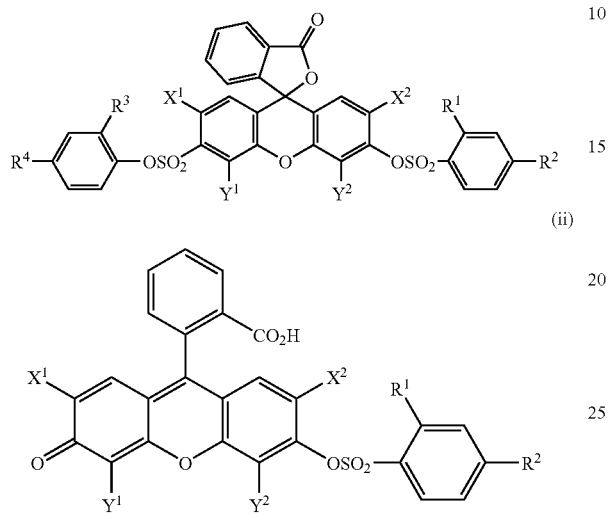

where, in the formulae (i) and (ii), each of $X^1$, $X^2$, $Y^1$ and $Y^2$ is a hydrogen atom, a straight or branched alkyl group having 1 to 6 carbon atoms or a halogen, $X^1$, $X^2$, $Y^1$ and $Y^2$ may be the same or different, $X^3$ is a straight or branched alkyl group having 1 to 6 carbon atoms or a trifluoromethyl group, each of $R^1$ and $R^3$ is a hydrogen atom, a nitro group, a methyl group, a chloro group or a methoxy group, $R^1$ and $R^3$ may be the same or different, each of $R^2$ and $R^4$ is a hydrogen atom, a nitro group, a trifluoromethyl group, a methyl group, an isopropyl group, a chloro group or a methoxy group, $R^2$ and $R^4$ may be the same or different, at least one of $R^1$ and $R^2$ is a nitro group, at least one of $R^3$ and $R^4$ is a nitro group, and in the case where, in the formula (iv), $X^3$ is a straight or branched alkyl group having 1 to 6 carbon atoms, both of $R^1$ and $R^2$ are groups except a hydrogen atom.

4. The sulfonate compound according to claim 1, represented by any of formulae into 1d, 1d, 3,4a to 4e, 8a, 8b and 8c below:

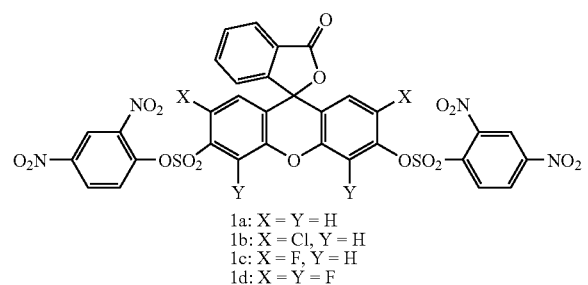

1a: X = Y = H
1b: X = Cl, Y = H
1c: X = F, Y = H
1d: X = Y = F

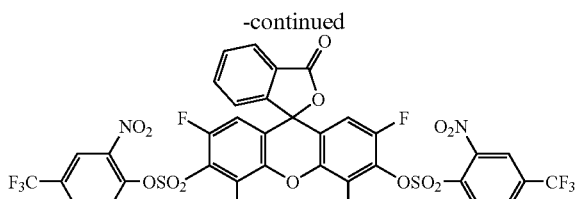

3

4a: $R^1 = NO_2$, $R^2 = CF_3$
4b: $R^1 = H$, $R^2 = =NO_2$
4c: $R^1 = NO_2$, $R^2 = H$
4d: $R^1 = NO_2$, $R^2 = OCH_3$
4e: $R^1 = OCH_3$, $R^2 = NO_2$

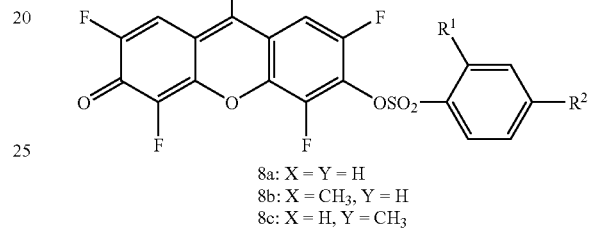

8a: X = Y = H
8b: X = CH_3, Y = H
8c: X = H, Y = CH_3

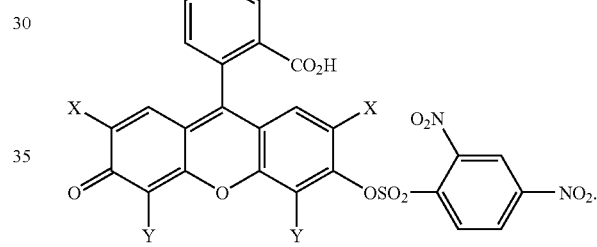

5. The sulfonate compound according to claim 1 represented by any of formulae 8a, 8b and 8c below:

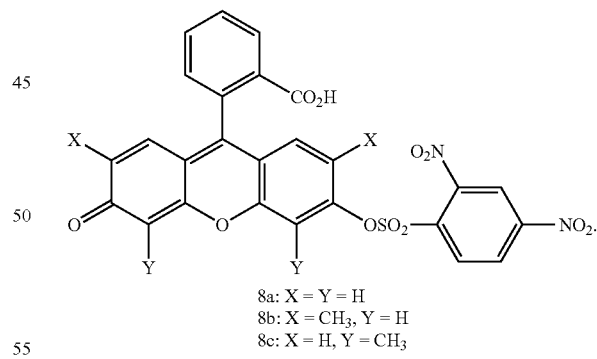

8a: X = Y = H
8b: X = CH_3, Y = H
8c: X = H, Y = CH_3

6. A fluorescent probe, consisting of the sulfonate compound represented by a formula (I) below, and forming a fluorescent compound upon cleavage of a covalent bond between an atomic group A-O and a sulfonyl group,

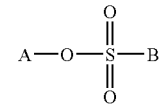

where, in the formula (I), an atomic group A-O is an atomic group that forms a fluorescent compound upon cleavage of a covalent bond between the atomic group A-O and a sulfonyl group, one or a plurality of atomic groups B—SO₃— are bonded to an atomic group A, B is a ring that is substituted by one or a plurality of electron-withdrawing groups, the electron-withdrawing group is at least one selected from the group consisting of an alkyl halide group, a nitro group and a cyano group, A is a formula represented by a formula (X-1) or (X-2) below,

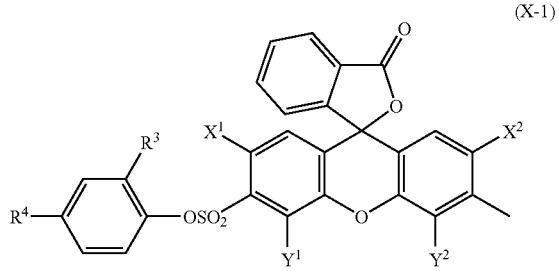
(X-1)

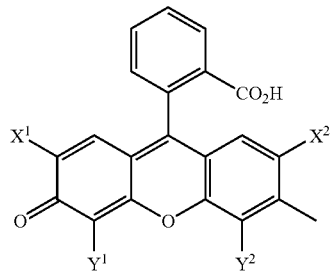
(X-2)

where, in the above formulae, each of $X^1$, $X^2$, $Y^1$ and $Y^2$ is hydrogen atom, a straight or branched alkyl group having 1 to 6 carbon atoms or a halogen, $X^1$, $X^2$, $Y^1$ and $Y^2$ may be the same or different, $R^3$ is a hydrogen atom, a nitro group, a methyl group, a chloro group or a methoxy group, and R4 is a hydrogen atom, a nitro group, a trifluoromethyl group, a methyl group, an isopropyl group, a chloro group or a methoxy group, and B may be the same or different in kind in the case where the plurality of B exist.

* * * * *